US008288368B2

(12) United States Patent
Allegretti et al.

(10) Patent No.: US 8,288,368 B2
(45) Date of Patent: Oct. 16, 2012

(54) OMEGA AMINOALKYLAMIDES OF R-2 ARYL PROPIONIC ACIDS AS INHIBITORS OF THE CHEMOTAXIS OF POLYMORPHONUCLEATE AND MONONUCLEATE CELLS

(75) Inventors: Marcello Allegretti, L'Aquila (IT); Riccardo Bertini, L'Aquila (IT); Valerio Berdini, L'Aquila (IT); Cinzia Bizzarri, L'Aquila (IT); Maria Candida Cesta, L'Aquila (IT); Vito Di Cioccio, L'Aquila (IT); Gianfranco Caselli, L'Aquila (IT); Fracesco Colotta, L'Aquila (IT); Carmelo Gandolfi, L'Aquila (IT); Janete Peloia Barroso Gandolfi, legal representative, Milan (IT); Giulio Agostino Gandolfi, legal representative, Milan (IT); Maria Carla Gandolfi, legal representative, Milan (IT); Arrigo Aldo Gandolfi, legal representative, Saronno (IT)

(73) Assignee: Dompé Pha.R.Ma S.p.A., L'Aquila (IT)

( * ) Notice: Subject to any disclaimer, the term of this patent is extended or adjusted under 35 U.S.C. 154(b) by 182 days.

(21) Appl. No.: 10/469,094

(22) PCT Filed: Feb. 25, 2002

(86) PCT No.: PCT/EP02/01974

§ 371 (c)(1),
(2), (4) Date: Jun. 16, 2004

(87) PCT Pub. No.: WO02/068377

PCT Pub. Date: Sep. 6, 2002

(65) Prior Publication Data

US 2005/0080067 A1 Apr. 14, 2005

(51) Int. Cl.
| A61K 31/397 | (2006.01) |
| A61K 31/55 | (2006.01) |
| A61K 31/445 | (2006.01) |
| A61K 31/40 | (2006.01) |
| A61K 31/165 | (2006.01) |
| A61K 31/195 | (2006.01) |

(52) U.S. Cl. ............ 514/183; 514/210.01; 514/217.11; 514/317; 514/426; 514/563; 514/616; 514/617; 540/605; 546/224; 548/557; 548/954; 562/450; 564/155

(58) Field of Classification Search ........................ None
See application file for complete search history.

(56) References Cited

U.S. PATENT DOCUMENTS

| 4,879,283 A | 11/1989 | Belzer et al. |
| 5,216,026 A | 6/1993 | Howbert |
| 5,886,044 A | 3/1999 | Widdowson et al. |
| 6,069,172 A | 5/2000 | Bertini et al. |
| 6,147,115 A | 11/2000 | Crowell et al. |
| 6,262,113 B1 | 7/2001 | Widdowson et al. |
| 6,348,032 B1 | 2/2002 | Sperl et al. |
| 6,355,682 B1 | 3/2002 | Weinberg |
| 6,410,584 B1 | 6/2002 | Pamukcu et al. |
| 6,774,212 B2 | 8/2004 | Han |
| 7,115,647 B2 | 10/2006 | Pamukcu et al. |
| 2005/0080067 A1 | 4/2005 | Allegretti et al. |

FOREIGN PATENT DOCUMENTS

| DE | 1949987 A1 | 4/1970 |
| DE | 2428223 A1 | 1/1975 |
| DE | 3128676 A1 | 4/1982 |
| GB | 1283943 A | 8/1972 |
| GB | 2080797 A | 2/1982 |
| JP | 49018875 A | 2/1974 |
| WO | WO-94/03209 | 2/1994 |
| WO | WO-00/24710 | 5/2000 |
| WO | WO-00/24710 A1 | 5/2000 |
| WO | 01/79189 A | 10/2001 |
| WO | WO-01/79189 A2 | 10/2001 |

OTHER PUBLICATIONS

Tsunematsu et al., "Synthesis and the Stereoselective Enzymatic Hydrolysis of Flurbiprofen-Basic Amino Acid Ethyl Esters," Journal of Drug Targeting, vol. 2, pp. 517-525 (1995).*

(Continued)

*Primary Examiner* — Sun Jae Loewe
(74) *Attorney, Agent, or Firm* — Birch, Stewart, Kolasch & Birch, LLP

(57) ABSTRACT

(R)-2-Arylpropionamide compounds of formula (I) are described.

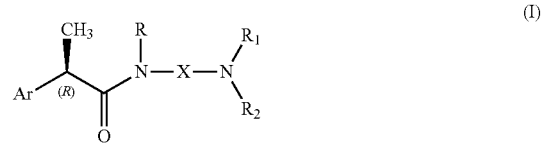

The process for their preparation and pharmaceutical preparations thereof are also described.

The 2-Arylpropionamides of the invention are useful in the prevention and treatment of tissue damage due to the exacerbate recruitment of polymorphonuclear leukocytes (leukocytes PMN) and of monocytes at the inflammatory sites. In particular, the invention relates to the R enantiomers of omega-aminoalkylamides of 2-aryl propionic acids, of formula (I), for use in the inhibition of the chemotaxis of neutrophils and monocytes induced by the C5a fraction of the complement and by other chemotactic proteins whose biological activity is associated with activation of a 7-TD receptor.

Selected compounds of formula (I) are dual inhibitors of both the C5a-induced chemotaxis of neutrophils and monocytes and the IL-8-induced chemotaxis of PMN leukocytes.

The compounds of the invention are used in the treatment of psoriasis, ulcerative cholitis, glomerular nephritis, acute respiratory insufficiency, idiopathic fibrosis, rheumatoid arthritis and in the prevention and the treatment of injury caused by ischemia and reperfusion.

5 Claims, No Drawings

OTHER PUBLICATIONS

Kawathekar et al., STN International, HCAPLUS Database, Columbus, OH, Accession No. 2000:407388 (2006).*
Rajasekaran et al., STN International, HCAPLUS Database, Columbus, OH, Accession No. 1999:669499 (2006).*
Kwiecien et al., STN International, HCAPLUS Database, Columbus, OH, Accession No. 1992:193838 (2006).*
Niewiadomski et al., STN International, HCAPLUS Database, Columbus, OH, Accession No. 1979:87209 (2006).*
Kawathekar, et al., "Synthesis, biological evaluation and QSAR analysis of some new derivatives of ketoprofen and flurbiprofen," Indian J. Pharm. Sciences, 60(6), p. 346-352 (1998).*
Rajasekaran, et al., "Synthesis and evaluation of antiinflammatory activity of ibuprofen analogs," Indian J. of Pharm. Sciences, 61(3), pp. 158-161 (1999).*
Kwiecien et al., "Synthesis of amides of phenylacetic acids," Polish Journal of Chemistry, 65(11), pp. 2057-2060 (1991).*
Niewiadomski et al., "Synthesis of 2-piperidinepropyl amides of expected antiinflammatory action," Polish Journal of Chemistry, 52(9), pp. 1805-1807 (1978).*
Tsunematsu et al., "Synthesis and the Stereoselective Enzymatic Hydrolysis of Flubiprofen-Basic Amino Acid Ethyl Esters," J. Drug Targeting, vol. 2, pp. 517-525 (1995).*
http://en.wikipedia.org/wiki/Enantiomeric.*
http://en.wikipedia.org/wiki/Chiral_resolution.*
http://en.wikipedia.org/wiki/Racemic.*
Francotte, J. Chrom. A, 906 (2001) 379-397.*
Tsunematsu H et al. Journal of Drug Targeting, Harwood Academic Publishers GMBH, DE, vol. 2, No. 6, 1995, pp. 517-525.
Kawathekar N. et al. Indian Journal of Pharmaceutical Sciences, XX, XX, vol. 60, No. 6, Nov. 1998, pp. 346-352.
Niewiadomski K. et al. Polish Journal of Chemistry, Polish Chemical Society, XX, vol. 4, No. 55, 1981, pp. 941-945.
Patrignani, P. et al., "Biochemical and Pharmacological Characterization of the Cyclooxygenase Activity of Human Blood Prostaglandin Endoperoxide Synthases," J.Pharm.Exp.Therapeutics, vol. 271, No. 3, pp. 1705-1712 (1994).
Van Damme, J. et al., "Identification by sequence analysis of chemotactic factors for monocytes produced by normal and transformed cells stimulated with virus, double-stranded RNA or cytokine," Eur.J.Immunol., vol. 19, pp. 2367-2373 (1989).
Office Action dated Apr. 8, 2009 for U.S. Appl. No. 10/544,396.
Office Action dated Oct. 21, 2009 for U.S. Appl. No. 10/544,396.
Notice of Allowance dated Jan. 29, 2010 for U.S. Appl. No. 10/544,396.
Office Action dated May 1, 2008 for U.S. Appl. No. 11/838,180.
Office Action dated Aug. 29, 2008 for U.S. Appl. No. 11/838,180.
Office Action dated Sep. 11, 2008 for U.S. Appl. No. 11/838,180.
Office Action dated Nov. 12, 2008 for U.S. Appl. No. 11/838,180.
Office Action dated Jul. 31, 2009 for U.S. Appl. No. 11/838,180.
Ducheyne,P. et al., "Biomaterials and Biomechanics 1983," Advances in Biomaterials, vol. 5, TOC, 6 pgs.
Bielstein Institut zur Forderung der Chemischen Wissenschaften, Frankfurt am Main, DE; retrieved from XFIRE Database accession No. 2107267 XP002254785 & DE 24 28 223 A, Jan. 2, 1975—ABS.
International Search Report in PCT/EP02/01974 dated Aug. 2, 2002.
International Preliminary Examination Report for PCT/EP02/01974 dated Aug. 11, 2003.
Kawathekar et al., "Synthesis, Biological Evaluation and Qsar Analysis of some new Derivatives of Ketoprofen and Flurbiprofen," India J. Pharm. Sci., vol. 60 (6), 1998, pp. 346-353.
Niewiadomski, K., et al., "Synthesis of 2-(4-Isobutylpiperidine)-Propyl Amides of Expected Antiinflammatory Action," Polish J. Chem., vol. 55, No. 941, (1981).
Shanbhag et al., "Ester and Amide Prodrugs of Ibuprofen and Naproxen: Synthesis, Anti-inflammatory Activity, and Gastrointestinal Toxicity," J. of Pharma. Sci., vol. 81, No. 2, Feb. 1992.
Tsunematsu, H. et al., "Synthesis and the Stereoselective Enzymatic Hydrolysis of Flurbiprofen-Basic Amino Acid Ethyl Esters," J. of Drug Targeting, vol. 2, 1995, pp. 517-525.

Acute Respiratory Distress Syndrome—http://en.wikipedia.org/wiki/Acute_respiratory_distress_syndrome.
Ischemia Reperfusion Therapy—www.ischemix.com/market/html.
Lung Ischemia Reperfusion Injury—http://healthsystem.virginia.edu/internet/tcv-lab/researchIIR.cfm.
Medscape Medical News—RA—http://www.medscape.com/viewarticle/537835_print.
Francotte, E. R., "Enantioselective chromatography as a powerful alternative for the prepareation of drug enantiomers," J. Chromatogr., vol. 906, pp. 379-397 (2001).
Li et al., "The Relationship Between Cytokines in MLC Supernatants and Acute Rejection After Renal Transplantation," Transplation Proceedings, vol. 32, No. 7, pp. 2531-2534 (2000).
Rajasekaran, A., et al., "Systhesis and Evalution of Antiinflammatory Activity of Ibuprofen Analogs," Indian J. Pharm. Sci., vol. 61, No. 3, pp. 158-161 (1999).
Kwiecien, H., et al., "Synthesis of Amides of Phenylacetic Acids," Polish J. Chem., vol. 65, pp. 2057-2060 (1991).
Niewiadomski, K., et al., "Synthesis of 2-Piperidinepropyl Amides of Expected Antiinflammatory Action," Polish J. Chem., vol. 52, pp. 1805-1807 (1978).
Crowell et al. (1992): STN International HCAPLUS databased, (Columbus, Ohio) Accession No. 1992: 151349.
Mita, K., et al., "p-Substituted benzylsulfonate salts," retrieved from STN Database accession No. 87:201093 CA XP002254774 & JP 52077030A Jun. 22, 1977, Database CA [Online] Chemical Abstracts Service, Columbus, Ohio, US—ABS.
Bielstein Institut zur Forderung der Chemischen Wissenschaften, Frankfurt am Main, DE; retrieved from XFIRE Database accession No. brn 2110387 XP002254775 & ACTA Chem Scan, vol. 15, p. 1081, 1961—ABS.
Bielstein Institut zur Forderung der Chemischen Wissenschaften, Frankfurt am Main, DE; retrieved from XFIRE Database accession No. 2118685 XP002254776 & Chem Ber, vol. 31, p. 1855-1898, ABS.
Bielstein Institut zur Forderung der Chemischen Wissenschaften, Frankfurt am Main, DE; retrieved from XFIRE Database accession No. 2208420 XP002254777 & J. Amer. Chem Soc., vol. 71, p. 2248, 1949—ABS.
Bielstein Institut zur Forderung der Chemischen Wissenschaften, Frankfurt am Main, DE; retrieved from XFIRE Database accession No. 2852262 XP002254778 & Bull Acad. Sci. USSR Div. Chem Sci, vol. 22, p. 874, 1973—ABS.
Bielstein Institut zur Forderung der Chemischen Wissenschaften, Frankfurt am Main, DE; retrieved from XFIRE Database accession No. 2360310 XP002254779 & J Amer Chem Soc, vol. 68, p. 139, 1946—ABS.
Bielstein Institut zur Forderung der Chemischen Wissenschaften, Frankfurt am Main, DE; retrieved from XFIRE Database accession No. 4649760 XP002254780 & J Amer Chem Soc, vo. 83, pp. 4636-4641, 1961—ABS.
Bielstein Institut zur Forderung der Chemischen Wissenschaften, Frankfurt am Main, DE; retrieved from XFIRE Database accession No. 4649760 XP002254781 & Tetrahedron Lett, vol. 28, pp. 1101-1104, 1987—ABS.
Bielstein Institut zur Forderung der Chemischen Wissenschaften, Frankfurt am Main, DE; retrieved from XFIRE Database accession No. 210679 XP002254782 & Yakugaku Zasshi, vol. 78, pp. 137, 140, 1958—ABS.
Bielstein Institut zur Forderung der Chemischen Wissenschaften, Frankfurt am Main, DE; retrieved from XFIRE Database accession No. 4742262 XP002254783 & Bull Chem Soc Jpn, vol. 64, pp. 1431-1433, 1991—ABS.
Bielstein Institut zur Forderung der Chemischen Wissenschaften, Frankfurt am Main, DE; retrieved from XFIRE Database accession No. 8977246 XP002254784 & Bioorg Med Chem, vol. 9, pp. 2955-2968, 2001—ABS.
Bielstein Institut zur Forderung der Chemischen Wissenschaften, Frankfurt am Main, DE; retrieved from XFIRE Database accession No. 2649523 XP002254786 & ACTA Chem Scan, vol. 14, pp. 1151-1160, 1960—ABS.

Bielstein Institut zur Forderung der Chemischen Wissenschaften, Frankfurt am Main, DE; retrieved from XFIRE Database accession No. 2652292 XP002254787 & J Chem Soc, pp. 3063-3069, 1960—ABS.

Han, Wei (2001): STN International HCAPLUS databased, (Columbus, Ohio) Accession No. 2001: 416971.

Office Action dated Oct. 6, 2004 for U.S. Appl. No. 10/250,465 (Patent 7,560,487).

Office Action dated Apr. 12, 2005 for U.S. Appl. No. 10/250,465 (Patent 7,560,487).

Office Action dated Nov. 30, 2005 for U.S. Appl. No. 10/250,465 (Patent 7,560,487).

Office Action dated Jun. 15, 2006 for U.S. Appl. No. 10/250,465 (Patent 7,560,487).

Office Action dated Dec. 15, 2006 for U.S. Appl. No. 10/250,465 (Patent 7,560,487).

Office Action dated Feb. 7, 2008 for U.S. Appl. No. 10/250,465 (Patent 7,560,487).

Office Action dated Sep. 29, 2008 for U.S. Appl. No. 10/250,465 (Patent 7,560,487).

Notice of Allowance dated Mar. 11, 2009 for U.S. Appl. No. 10/250,465 (Patent 7,560,487).

Kutukculer et al., "The Value of Posttransplant Monitoring of Interleukin (IL)-2, IL-3, IL-4, IL-6, IL-8, And Soluble CD23 in the Plasma of Renal Allograft Recipients," Transplantation, vol. 59, No. 3, Feb. 15, 1995.

International Search Report for PCT/EP02/01974.

IPER for PCT/EP02/01974.

Partial Search Report EP 03 005 783.0.

Cabré, F., et al., "Analgesic, Antiinflammatory, and Antipyretic Effects of S(+)-Ketoprofen in Vivo," J. Clin, Pharmacol., vol. 38, pp. 3S-10S (1998).

Carabaza, A., et al., "Stereoselective Inhibition of Inducible Cyclooxygenase by Chiral Nonsteroidal Antiinflammatory Drugs," J. Clin. Pharmacol., vol. 36, pp. 505-512 (1996).

* cited by examiner

US 8,288,368 B2

OMEGA AMINOALKYLAMIDES OF R-2 ARYL PROPIONIC ACIDS AS INHIBITORS OF THE CHEMOTAXIS OF POLYMORPHONUCLEATE AND MONONUCLEATE CELLS

This application is the national phase under 35 U.S.C. §371 of PCT International Application No. PCT/EP02/01974 which has an International filing date of Feb. 25, 2002, which designated the United States of America.

The present invention relates to omega-aminoalkylamides of (R)2-aryl-propionic acids as inhibitors of the chemotaxis of polymorphonucleate and mononucleate cells. In particular, the invention relates to inhibitors of the C5a—induced chemotaxis of polymorphonucleate leukocytes and monocytes, which are used in the treatment of pathologies including psoriasis, rheumatoid arthritis and injury caused by ischemia and reperfusion.

INTRODUCTION AND BACKGROUND OF THE INVENTION

Animal studies show that some aminoalkylester and amide prodrugs of racemic ibuprofen and naproxen, in particular some N-(3-diethylaminopropyl)amides, exhibit analgesic and antiinflammatory activity significantly better than the parent compounds, even though "in vitro" they have been found to be poor inhibitors of the synthesis of prostaglandins. All these prodrugs, except a glycine amide, have also been found to be significantly less irritating to the gastric mucosa than their precursor free acids. (Shanbhag V R et al., J. Pharm. Sci., 81, 149, 1992 and references 8-19) therein cited.

Piketoprofen [(±)2-(3-benzoylphenyl)-N-(4-methyl-2-pyridinyl)propionamide] and Amtolmetin Guacil (also named guaiacol ester of tolmetinglycinamide, Eufans) are further examples of non steroidal antiinflammatory (NSAI) prodrugs in current therapeutic use. Moderate antiinflammatory activity, minor side effects and good gastro-intestinal tolerance are reported for a series or N-[2-(1-piperidinyl)propyl]amides of some NSAI drugs such as racemic ibuprofen, indomethacin, p-chlorobenzoic acid, acetylsalicyclic acid, diacetylgentisic acid and adamantane-1-carboxylic acid (Nawladonski F. and Reewuski, Pol. J. Chem., 52, 1805, 1978). Other amides of racemic 2-arylpropionic acids have been disclosed by S. Biniecki et al., [PL 114050 (31. 01. 1981)], H. Akguen et al., [Arzneim-Forsch., 46, 891, 1986] and by G. L. Levitt et al., [Russ. J. Org. Chem., 34, 346, 1998].

Anti-inflammatory and analgesic potencies "in vivo", comparable and sometimes greater than those of the precursor free acids, along with decreased number of gastric lesions, have been reported for some N-3-[(1-piperidinyl)propyl] amides of racemic ketoprofen and flurbiprofen and for certain Mannich bases obtained reacting their amides with formaldehyde and secondary amines such as morpholine, piperidine, dicyclohexylamine, dimethylamine, diethylamine, dibenzylamine and dibutylamine (N. Kawathekar et al., Indian J. Pharm. Sci., 60, 346, 1998).

International patent application, WO 00/40088, has recently reported that the mere conversion to an amide derivative of a 2-arylacetic and/or 2-arylpropionic acid is enough to change a selective COX-1 inhibitor into a COX-2 selective inhibitor which explains the decreased gastrolesivity of said amides, for a long time believed to be only NSAI prodrugs.

In the past, inhibition of the cyclooxygenase enzymes was known to be proper of the S enantiomer of 2-arylpropionic acids alone, joined together with the portion of R CoA-thioester suffering bioconversion "in vivo". Therefore, the poor correlation between enzymatic inhibition "in vitro" and analgesic effects "in vivo" found for certain R,S 2-arylpropionic acids (Brune K. et al., Experientia, 47, 257, 1991) has induced to presume that alternative mechanisms, such as inhibition of transcription of the kB-nuclear transcription factor (NF-kB) and/or inhibition of neutrophil chemotaxis induced by interleukin 8 (IL-8), can be operating.

R enantiomers of flurbiprofen, ketoprofen, naproxen, thiaprofen and phenoprofen are, in fact, disclosed in WO 00/40088 as inhibitors of the NF-kB transcription factor activation and claimed to be useful in the treatment of NF-kB dependent diseases (asthma, tumor, shock, Crohn'disease and ulcerative colitis, arteriosclerosis, etc).

IL-8 is an important mediator of inflammation and has been shown to be a potent chemotactic/cell activator for polymorphonucleate neutrophils and basophils (PMNs), and T lymphocytes. Cellular sources of IL-8 include monocytes, PMNs, endothelial cells, epithelial cells, and keratinocytes when stimulated by factors such as lipopolysaccaride, IL-1 and TNF-$\alpha$. On the other hand, the complement fragment C5a, in addition to being a direct mediator of inflammation, has been found to induce both IL-8 synthesis and high level of IL-8 release from monocytes. The quantity of IL-8 recovered from C5a activated monocytes in peripheral blood mononuclear cells is up to 1,000 fold greater than that released from comparable numbers of PMNs under similar conditions. Therefore IL-8 released from C5a-activated monocytes may play a significant role in expanding and prolonging cellular infiltration and activation at the sites of infection, inflammation, or tissue injury (Ember J. A. et al., Am. J. Pathol., 144, 393, 1994).

In response to immunologic and infective events, activation of the complement system mediates amplification of inflammatory response both via direct membrane action and via release of a series of peptide fragments, generally known as anaphylatoxins, generated by enzymatic cleavage of the C3, C4 and C5 complement fractions. These peptides include C3a, C4a, both made of 77 aminoacids; in turn, C5 convertase cleaves the C5 complement fraction to give the glycoprotein C5a of 74 aminoacids.

Anaphilatoxins contribute to the spreading of the inflammatory process by interaction with individual cell components; their common properties are cellular release of vasoactive amines and lysosomal enzymes, contraction of smooth muscle and increased vascular permeability. Moreover, C5a causes chemotaxis and aggregation of neutrophils, stimulates the release of leukotrienes and of oxidized oxygen species, induces the transcription of IL-1 in macrophages and the production of antibodies.

The C5a peptide fragment of the complement has been defined as the "complete" pro-inflammatory mediator. On the contrary, other inflammatory mediators such as selected cytokines (IL-8, MCP-1 and RANTES, for example) are highly selective towards self-attracted cells, while histamine and bradykinin are only weak chemotactic agents.

Convincing evidences support the involvement of C5a, "in vivo", in several pathological conditions including ischemia/reperfusion, autoimmune dermatitis, membrane-proliferative idiopathic glomerulonephritis, airway iperresponsiveness and chronic inflammatory diseases, ARDS and COPD, Alzheimer'disease, juvenile rheumatoid arthritis (N. P. Gerard, Ann. Rev. Immunol., 12, 755, 1994).

In view of the neuro-inflammatory potential of C5a/C5a-desArg generated by both local complement production and amyloid activation joined with astrocyte and microglia chemotaxis and activation directly induced by C5a, complement inhibitors have been proposed for the treatment of neurological diseases such as Alzheimer'disease (McGeer & McGeer P. L., Drugs, 55, 738, 1998).

Therefore, the control of the local synthesis of complement fractions is considered of high therapeutic potential in the treatment of shock and in the prevention of rejection (multiple organ failure and hyperacute graft rejection) (Issekutz A. C. et al., Int. J. Immunopharmacol, 12, 1, 1990; Inagi R. et at., Immunol. Lett., 27, 49, 1991). More recently, inhibition of complement fractions has been reported to be involved in the prevention of native and transplanted kidney injuries taking account of complement involvement in the pathogenesis of both chronic interstitial and acute glomerular renal injuries. (Sheerin N. S. & Sacks S. H., Curr. Opinion Nephrol. Hypert., 7, 395, 1998).

Genetic engineering and molecular biology studies led to the cloning of complement receptors (CRs) and to the production of CRs agonists and antagonists. The recombinant soluble receptor CR1 (sCR1), that blocks enzymes activating C3 and C5, has been identified as a potential agent for the suppression of C activation on ischemia/reperfusion injury (Weisman H. F. et al., Science, 239, 146, 1990; Pemberton M. et al., J. Immunol., 150, 5104, 1993).

The cyclic peptide F-[OPdChWR], is reported to antagonize the C5a binding to its CD38 receptor on PMNs and to inhibit C5a-dependent chemotaxis and cytokine production by macrophages and rat neutropenia induced by C5a and LPS stimulation (Short A. et al., Br. J. Pharmacol., 126, 551, 1999; Haynes D. R. et al., Biochem. Pharmacol., 60, 729, 2000). Both C5aR antagonist CGS 27913 and its dimer CGS 32359 are reported to inhibit, "in vitro", C5a binding to neutrophil membranes, intracellular $Ca^{2+}$ mobilization, lysozyme release, neutrophil chemotaxis and dermal edema in rabbits (Pellas T. C. et al., J. Immunol., 160, 5616, 1998).

Finally, selection from phage libraries with the "phage display" technique has led to the isolation of a specific C5aR antagonist able to decrease inflammatory responses in diseases mediated by immuno-complexes and in ischemia and reperfusion injuries (Heller T. et al., J. Immunol., 163, 985, 1999).

Despite their therapeutic potential, only two of the above discussed C5a antagonists have demonstrated activity "in vivo"; furthermore, their use is therapeutically limited by their peptidic nature. (Pellas T. C., Wennogle P., Curr. Pharm. Des., 10, 737, 1999).

Characteristic neutrophil accumulation can be observed in some pathologic conditions, for example in the highly inflamed and therapeutically recalcitrant areas of psoriatic lesions. Neutrophils are chemotactically attracted and activated by the sinergistic action of chemokines, IL-8 and Gro-a released by the stimulated keratinocytes, and of the C5a/C5a-desArg fraction produced via the alternative complement pathway activation (T. Terui et al., Exp. Dermatol., 9, 1, 2000). In many circustances it is, therefore, highly desirable to combine inhibition of the chemotaxis induced by C5a and inhibition of the chemotaxis induced by IL-8 in one single agent.

Non-peptidic antagonists of complement fractions have also been prepared, for example substituted-4,6-diamino-quinolines. In particular, [N,N"-bis-(4-amino-2-methyl-6-quinolyl)]urea and [6-N-2-chlorocynnamoyl)-4,6-diamino-2-methylquinoline] have been found selective C5R antagonists, their $IC_{50}$ ranging between 3.3 and 12 μg/mL (Lanza T. J. et al., J. Med. Chem., 35, 252, 1992).

Some serine-protease inhibitors [nafamostat mesilate (FUT 175) and certain analogs] have been recently reported to be inhibitors of both complement activation and C3a/C5a production (Ueda N. et al., Inflammation Res. 49, 42, 2000).

U.S. Pat. No. 6,069,172 reports the use of pharmaceutical formulations of R(-)ketoprofen ammonium salts for the inhibition of neutrophil chemotaxis induced by IL-8.

WO 00/24710 discloses N-acylsulfonamides of R(-)2-aryl-propionic acids as inhibitors of IL-8 dependent polymorphonucleate leukocytes chemotaxis.

Two recent patent applications [WO 01/58852 and WO 01/79189] disclose certain R-2-aryl-propionamides and R-2-(aminophenyl)propionamides useful for preventing leukocyte activation induced by IL-8.

We have recently observed that the mere formal reduction of the hetero-aromatic ring of certain R 2-aryl-N-(pyridinyl) propionamides causes marked loss of potency (1 or 2 logarithmic order) in the capacity to inhibit PMN neutrophil chemotaxis induced by IL-8. Unexpectedly, the related R 2-aryl-N-(piperidinyl)propionamides have been found to be potent inhibitors of chemotaxis of human PMN leukocytes and monocytes induced by the C5a fraction of the complement.

These unexpected findings have originated a novel family of omega-aminoalkylamides of R-2-aryl-propionic acids which are able to inhibit the chemotactic activity induced by C5a and other chemotactic proteins whose biological activity is associated with activation of a 7-membered-domain receptor (7-TD) homologous to the receptor of C5a (for example, the C3a receptor and the CXCR2 receptor; Neote K. et al., Cell, 72, 415, 1993; Tometta M. A., J. Immunol., 158, 5277, 1997).

BRIEF DESCRIPTION OF THE INVENTION

It is the object of the present invention a novel class of omega-aminoalkylamides of R-2-aryl-propionic acids and pharmaceutical compositions containing them. The position "omega" in the alkyl chain refers to the furthest carbon atom starting from the N atom of the amide group to which said alkyl is linked. Such amides are useful in the inhibition of the chemotactic activation induced by C5a and by other chemotactic proteins whose biological activity is associated with the activation of 7-transmembrane domains (7-TD) receptors homologous to the C5a receptor. In particular such amides are useful in the inhibition of the chemotactic activation of polymorphonucleate leukocytes, monocytes and lymphocytes T induced by the fraction C5a of the complement and in the treatment of pathologies related to said activation.

DETAILED DESCRIPTION OF THE INVENTION

The following paragraphs provide definitions of outstanding chemical moieties that make up the compounds according to the invention and are intended to apply uniformly throughout the specification and claims unless an otherwise expressly set out definition provides a broader definition.

The term "alkyl" refers to monovalent alkyl groups having preferably 1 to 6 carbon atoms. These terms are exemplified by groups such as methyl, ethyl, n-propyl, isopropyl, n-butyl, isobutyl, tert-butyl, and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, biphenyl, naphthyl, phenantrenyl and the like.

"Alkenyl" refers to alkenyl groups preferably having from 2 to 5 carbon atoms and having one or more sites of alkenyl unsaturation. Preferred alkenyl groups include ethenyl ($-CH=CH_2$), n-2-propenyl (allyl, $-CH_2CH=CH_2$) and the like.

"Alkylene", "Alkenylene", Alkynylene" refer to groups disubstituted at both ends. Preferred groups include methylene, ethylene, propylene, and like.

"Substituted or non-substituted": unless otherwise constrained by the definition of the individual substituent, the above set out groups, like "alkyl", "alkenyl", "aryl" groups etc. can optionally be substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", primary, secondary or tertiary amino groups or quarternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Within the framework of this invention, said "substitution" is meant to also comprise situations where neighbouring substituents undergo ring closure, in particular when vicinal functional substituents are involved, thus forming e.g. lactams, lactons, cyclic anhydrides or cycloalkanes, but also acetals, thioacetals, aminals formed by ring closure for instance in an effort to obtain a protective group.

"Pharmaceutically acceptable salts" refers to salts or complexes of the below-identified compounds of formula I that retain the desired biological activity. Examples of such salts include, but are not restricted to, acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid.

Examples of salts also include acid addition salts formed with inorganic bases such as sodium hydroxyde and with organic bases such as tromethamine, L-lysine, L-arginine and the like.

The present invention provides (R)-2-aryl-propionamide compounds of formula (I),

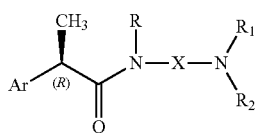

wherein
Ar represents a substituted or non-substituted aryl group;
R represents hydrogen, $C_1$-$C_4$ alkyl, $C_2$-$C_4$ alkenyl, $C_2$-$C_4$ alkynyl, optionally substituted by a $CO_2R_3$ group, wherein $R_3$ represents hydrogen or a linear or branched $C_1$-$C_6$ alkyl group or a linear or branched $C_2$-$C_6$ alkenyl group;
X represents:
linear or branched $C_1$-$C_6$ alkylene, $C_4$-$C_6$ alkenylene, $C_4$-$C_6$ alkynylene, optionally substituted by a $CO_2R_3$ group or by a $CONHR_4$ group wherein $R_4$ represents hydrogen, linear or branched $C_2$-$C_6$ alkyl or an $OR_3$ group, $R_3$ being defined as above;
a $(CH_2)_m$—B—$(CH_2)_n$, group, optionally substituted by a $CO_2R_3$ or $CONHR_4$ group, as defined above, wherein B is an oxygen or sulfur atom, m is zero or an integer from 2 to 3 and n is an integer from 2 to 3; or B is a CO, SO or CONH group, m is an integer from 1 to 3 and n is an integer from 2 to 3;
or X together with the nitrogen atom of the omega-amino Croup to which it is bound and with the $R_1$ group forms a non-aromatic nitrogen containing 3-7 membered heterocyclic, monocyclic or polycyclic ring wherein the nitrogen atom has a substituent Rc, where Rc represents hydrogen, $C_1$-$C_4$ alkyl, $C_1$-$C_4$ hydroxylalkyl, $C_1$-$C_4$ acyl, substituted or non-substituted phenyl, diphenylmethyl;
$R_1$ and $R_2$ are independently hydrogen, linear or branched $C_1$-$C_6$ alkyl, optionally interrupted by an O or S atom, a $C_3$-$C_7$ cycloalkyl, $C_3$-$C_6$ alkenyl, $C_3$-$C_6$-alkynyl, aryl-$C_1$-$C_3$-alkyl, hydroxy-$C_2$-$C_3$-alkyl group;
or $R_1$ and $R_2$ together with the N atom to which they are bound, form a nitrogen containing 3-7 membered heterocyclic ring of formula (II)

wherein Y represents a single bond, $CH_2$, O, S, or a N-Rc group as defined above and p represents an integer from 0 to 3;
or, $R_1$ being as defined above, $R_2$ represents a group of formula (III):

wherein $R_a$ is hydrogen and $R_b$ is hydrogen, hydroxy, $C_1$-$C_4$-alkyl or an $NR_dR_e$ group wherein $R_d$ and $R_e$, are each independently, hydrogen, $C_1$-$C_4$-alkyl or phenyl;
or $R_a$ and $R_b$, together with the nitrogen atoms to which they are bound, form a 5-7 membered heterocyclic ring, monocyclic or fused with a benzene, pyridine or pyrimidine ring;
with the proviso that when Ar is a 4-diphenyl residue and X is an ethylene or propylene residue, $R_1$ and $R_2$ are not ethyl;
with the further proviso that, when Ar is a 4-(2-fluoro)diphenyl residue, and X is butylene substituted by a $CO_2H$ group, $R_a$ and $R_b$ are not hydrogen;
and with the further proviso that, when Ar is phenyl and X is butylene, R1 and R2 together are not a N-(2-methoxy phenyl)piperazine.

In addition, the present invention further provides (R)-2-aryl-propionamide compounds of formula (I)

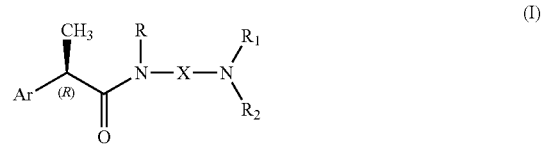

wherein
Ar represents a substituted or non-substituted aryl group;
R represents hydrogen, $C_1$-$C_4$ alkyl, $C_2$-$C_4$ alkenyl, $C_2$-$C_4$ alkynyl, optionally substituted by a $CO_2R_3$ group, wherein $R_3$ represents hydrogen or a linear or branched $C_1$-$C_6$ alkyl group or a linear or branched $C_2$-$C_6$ alkenyl group;
X represents:
linear or branched $C_1$-$C_6$ alkylene, $C_4$-$C_6$ alkenylene, $C_4$-$C_6$ alkynylene, optionally substituted by a $CO_2R_3$ group or by a CONHR$_4$ group wherein R$_4$ represents hydrogen, linear or branched C$_2$-C$_6$ alkyl or an OR$_3$ group, R$_3$ being defined as above;

a (CH$_2$)$_m$—B—(CH$_2$)$_n$, group, optionally substituted by a CO$_2$R$_3$ or CONHR$_4$ group, as defined above, wherein B is an oxygen or sulfur atom, m is zero or an integer from 2 to 3 and n is an integer from 2 to 3; or B is a CO, SO or CONH group, m is an integer from 1 to 3 and n is an integer from 2 to 3;

or X together with the nitrogen atom of the omega-amino group to which it is bound and with the R$_1$ group forms a non-aromatic nitrogen containing 3-7 membered heterocyclic, monocyclic or polycyclic ring wherein the nitrogen atom has a substituent Rc, where Rc represents hydrogen, C$_1$-C$_4$ alkyl, C$_1$-C$_4$ hydroxylalkyl, C$_1$-C$_4$ acyl, substituted or non-substituted phenyl, diphenylmethyl;

R$_1$ and R$_2$ are independently hydrogen, linear or branched C$_1$-C$_6$ alkyl, optionally interrupted by an O or S atom, a C$_3$-C$_7$ cycloalkyl, C$_3$-C$_6$ alkenyl, C$_3$-C$_6$-alkynyl, aryl-C$_1$-C$_3$-alkyl, hydroxy-C$_2$-C$_3$-alkyl group;

or R$_1$ and R$_2$ together with the N atom to which they are bound, form a 3-7 membered nitrogen heterocyclic ring of formula (II)

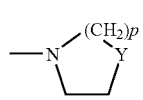

(II)

wherein Y represents a single bond, CH$_2$, O, S, or a N-Rc group as defined above and p represents an integer from 0 to 3;

or, R$_1$ being as defined above, R$_2$ represents a group of formula (III):

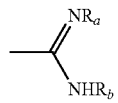

(III)

wherein R$_a$ is hydrogen and R$_b$ is hydrogen, hydroxy, C$_1$-C$_4$-alkyl or an NR$_d$R$_e$ group wherein R$_d$ and R$_e$, are each independently, hydrogen, C$_1$-C$_4$-alkyl or phenyl;

or R$_a$ and R$_b$, together with the nitrogen atoms to which they are bound, form a 5-7 membered heterocyclic ring, monocyclic or fused with a benzene, pyridine or pyrimidine ring;

for use as inhibitors of the C5a-induced chemotaxis of polymorphonucleate leukocytes and monocytes.

Pharmaceutically acceptable salts of the compounds of formula (I) are also within the scope of the present invention.

Examples of aryl groups preferably comprise:

a) an Ar$_a$ mono- or poly-substituted aryl group, or the most common heterocyclic rings found 2-aryl-propionic acids in current therapeutic use: alminoprofen, benoxaprofen, carprofen, fenbufen, fenoprofen, flurbiprofen, ibuprofen, indoprofen, ketoprofen, loxoprofen, naproxen, pirprofen and its dehydro and dihydro derivatives, pranoprofen, surprofen, tiaprofenic acid, zaltoprofen;

b) an aryl-hydroxymethyl-aryl group of formula (IVa) deriving from the reduction of the phenone carbonyl of 2-aryl-propionic acids: ketoprofen, surprofen, thiaprofenic acid, both as single (S',R) and/or (R',R) diastereoisomer and as diastereoisomeric mixture,

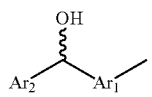

(IVa)

wherein, when Ar$_2$ is phenyl, Ar$_1$ is selected from the group consisting of phenyl and thien-2-yl and, when Ar$_1$ is phenyl, Ar$_2$ is selected from the group consisting of phenyl, 4-thienyl, pyridyl, c) an aryl of formula (IVb):

(IVb)

wherein

Ar$_b$ is a phenyl mono- and poly-substituted by optionally substituted hydroxy, mercapto, C$_1$-C$_3$-alcoxy, C$_1$-C$_3$-alkylthio, chlorine, fluorine, trifluoromethyl, nitro, amino, C$_1$-C$_7$-acylamino optionally substituted; and φ is hydrogen; a linear or branched C$_1$-C$_5$ alkyl, C$_2$-C$_5$-alkenyl or C$_2$-C$_5$-alkynyl residue by C$_1$-C$_3$-alkoxycarbonyl, substituted or non-substituted phenyl, 2-, 3- or 4-pyridyl, quinolin-2-yl; a C$_3$-C$_6$-cycloalkyl group; 2-furyl; 3-tetrahydrofuryl; 2-thiophenyl; 2-tetrahydrothiophenyl or a residue of formula (IVc)

(IVc)

wherein A is a C$_1$-C$_5$-dialkylamino group, a C$_1$-C$_8$-(alcanoyl, cycloalcanoyl, arylalcanoyl)-C1-C5-alkylamino group, for example dimethyamino, diethylamino, methyl-N-ethyl-amino, acetyl-N-methyl-amino, pivaloyl-N-ethyl-amino; a nitrogen containing 5-7 membered monocyclic ring optionally containing one or two double bonds and optionally an additional heteroatom separated by at least 2 carbon atoms from the atom of N, so as to form, for example, a 1-pyrrolidino, 2,5-dihydro-pyrrol-1-yl, 1-pyrrol, 1-piperidino, 1-piperazino-4-non-substituted or 4-substituted (methyl, ethyl, 2-hydroxyethyl, benzyl, benzhydril or phenyl), 4-morpholino, 4-3,5-dimethyl-morpholino, 4-thiomorpholino group; or alternatively, a residue of formula (IVd)

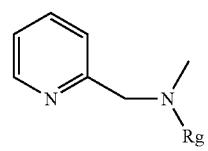

(IVd)

wherein Rg is hydrogen, C$_1$-C$_3$-alkyl or the residue of a C$_1$-C$_3$-alcanoic acid;

q is zero or the integer 1, d) a 2-(phenylamino)-phenyl of formula (IV e):

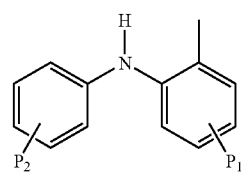

(IVe)

wherein $P_1$ and $P_2$ indicate that the two phenyl groups may be substituted independently, with one or more $C_1$-$C_4$-alkyl groups, $C_1$-$C_3$-alkoxy groups, chlorine, fluorine and/or trifluoromethyl.

Preferred compounds of the invention are compounds wherein:
R is hydrogen,
X is:
a linear alkylene optionally substituted at $C_1$ by a —CO2$R_3$ group as defined above;
a linear alkylene optionally substituted at $C_1$ by a —CONH$R_4$ group wherein $R_4$ is OH;
2-butynylene, cis-2-butenylene, trans-2-butenylene;
3-oxa-pentylene, 3-thio-pentylene, 3-oxa-hexylene, 3-thio-hexylene;
$(CH_2)_m$—CO—NH—$(CH_2)_n$-wherein m and n are each independently an integer from 2 to 3;
(CHR')—CONH—$(CH_2)_n$ wherein n is an integer from 2 to 3 and R' is a methyl, in absolute configuration R or S;
or X, together with the N atom of the omega-amino group, forms a nitrogen containing cycloaliphatic ring, preferably 1-methyl-piperidin-4-yl or 1,5-tropan-3-yl.

Preferred compounds are also those wherein $NR_1R_2$ represents an $NH_2$ group, dimethylamino, diethylamino, diisopropylamino, 1-piperidinyl, 4-morpholyl, 4-thiomorpholyl or $R_1$ and $R_2$ together form a residue of guanidine, aminoguanidine, hydroxyguanidine, 2-amino-3,4,5,6-tetrahydropyrimidyl, 2-amino-3,5-dihydro-imidazolyl.

Examples of particularly preferred aryl groups comprise: 4-isobutylphenyl, 4-cyclohexylmethylphenyl, 4-(2-methyl)allyl-phenyl, 3-phenoxyphenyl, 3-benzoyl-phenyl, 3-acetyl-phenyl, the single diastereoisomers (R) (S) and the diastereoisomeric mixture (R,S) of 3-$C_6H_5$—CH(OH)-phenyl, 3-$CH_3$—CH(OH)-phenyl, 5-$C_6H_5$—CH(OH)-thienyl, 4-thienyl-CH(OH)-phenyl, 3-(pyrid-3-yl)-CH(OH)-phenyl, 5-benzoyl-thien-2-yl, 4 thienoyl-phenyl, 3-nicotinoyl-phenyl, 2-fluoro-4-phenyl, 6-metoxy-2-naphthyl, 5-benzoyl-2-acetoxy-phenyl and 5-benzoyl-2-hydroxy-phenyl.

Particularly preferred aryl groups of formula (IVb) are phenyl groups 3-substituted by: isoprop-1-en-1-yl, isopropyl, pent-2-en-3-yl; pent-3-yl; 1-phenylethylen-1-yl; α-methylbenzyl.

Particularly preferred aryls of formula (IVc) are 4-(pyrrolidin-1-yl)-methyl-phenyl, 3-chloro-4-(pyrrolidin-1-yl)-methyl-phenyl, 3-chloro-4-(2,5-dihydro-1-H-pyrrol-1-yl)-methyl-phenyl, 3 chloro-4-(thiomorpholin-4-yl)phenyl; 3-chloro-4-(piperidin-1-yl)-phenyl, 4-((N-ethyl-N-quinolin-2-yl-methylamino)-methyl)phenyl, 3-chloro-4-(morpholin-4-yl)-phenyl.

Particularly preferred aryls of formula (IVe) are 2-(2,6-dichloro-phenyl-amino)-phenyl; 2-(2,6-dichloro-phenyl-amino)-5-chloro-phenyl; 2-(2,6-dichloro-3-methyl-phenyl-amino)-phenyl; 2-(3-trifluoromethyl-phenyl-amino)-phenyl.

Particularly preferred compounds of the invention are:
(R)-2-[(4-isobutyl)phenyl]-N-(3-dimethylaminopropyl)propionamide;
(R)-2-[(4-isobutyl)phenyl]-N-(4-dimethylaminobutyl)-propionamide hydrochloride;
(R)-2-[(4-isobutyl)phenyl]-N-(3-N-morpholinylpropyl)propionamide;
(R)-2-[(4-isobutyl)phenyl]-N-(2-dimethylaminoethyl)propionamide;
(R)-2-[(4-isobutyl)phenyl)-propionyl]-N-[2-(4-methyl-piperazin-1-yl)ethyl]propionamide;
(R)-N-(exo-8-methyl-8-aza-bicyclo[3,2,1]oct-3-yl)-2-[(4-isobutylphenyl)-propionamide;
(R)-2-[(4-isobutyl)phenyl]-N-(3-N-thiomorpholinylpropyl)propionamide;
(R)-2-[(4-isobutyl)phenyl]-N-[4-(N'-methyl)piperidinyl]propionamide hydrochloride;
(R),(S')-2-[(4-isobutyl)phenyl]-N-(1-carboxy-2-dimethylaminoethyl)-propionamide;
(R),(S')-2-[(4-isobutyl)phenyl]-N-[(1-carboxy-4-piperidin-1-yl)butyl]propionamide;
(R),(S')-2-[(4-isobutyl)phenyl]-N-(1-carboxy-4-aminobutyl)propionamide;
(R)-2-(4-isobutyl)phenyl-N-[2-(dimethylaminoethyl)aminocarbonylmethyl]propionamide hydrochloride;
2-(2,6-dichlorophenylamino)-phenyl-N-(3-dimethylaminopropyl)propionamide;
(R),(R',S')-3-[3-(α-methyl)benzyl]phenyl-N-(3-dimethylaminopropyl)-propionamide;
(R)-2-[(3-isopropyl)phenyl]-N-(3-dimethylaminopropyl)propionamide;
(R)-2-[3-(pent-3-yl)phenyl]-N-(3-dimethylaminopropyl)propionamide;
(R)-2-[(4-isobutyl)phenyl]-N-(3-guanidylpropyl)propionamide;
(R)-2-[(4-isobutyl)phenyl]-N-[(3-hydroxy-guanidyl)propyl]propionamide;
(R)-2-[(4-isobutyl)plenyl]-N-[(3-amino-guanidyl)propyl]propionamide;
(R)-2-[(4-isobutyl)phenyl]-N-[3-(2-amino-2-imidazoline)propyl]propionamide;
(R)-2-[(4-isobutyl)phenyl]-N-[N-methyl-N-(2-hydroxyethyl)aminoethoxy]propionamide;
(R),(S')-2-[(4-isobutyl)phenyl]-N-[1-carboxy-5-aminopentyl]propionamide.

The preparation of the compounds of formula (I) has been carried out using known methods such as the reaction of an activated form of an R-2-arylpropionic acid of formula (V) with an amine of formula (VI) in non-racemizing conditions, preferably in the presence of a molar excess of a base:

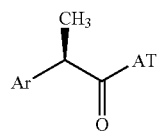

(V)

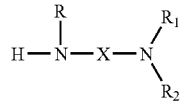

(VI)

wherein:
AT is the residue activating the carboxy group. Examples of activated forms of 2-arylpropionic acids of formula (V, AT=OH) are chlorides (AT=Cl), imidazolides (AT=1-imidazole), phenol esters such as p-nitrophenol (AT=p-NO2-C6H4O—) or activated forms obtained by reaction in the presence of 1-hydroxybenzotriazole (HOBZ) or of a carbodiimide, for example dicyclohexylcarbodiimide.
Ar, R, X, $R_1$ and $R_2$ are as defined above, optionally protected, where necessary.

The reaction of the activated form of a 2-aryl-propionic acid of formula (V) with a protected amine of formula (VI), is usually carried out at room temperature, using conventional protic or aprotic solvents and/or their mixtures, preferably anhydrous solvents, for example esters such as methyl acetate, ethyl acetate, ethyl formate, nitrites such as acetonitrile, linear or cyclic ethers such as ethyl ether, sulfolane, dioxane, tetrahydrofuran, amides such as dimethylformamide, formamide, halogenated solvents such as dichloromethane, aromatic hydrocarbons such as toluene, chlorobenzene or hetero-aromatic hydrocarbons such as pyridine and picoline. The reactions may be carried out in the presence of a base; preferred inorganic bases are alkaline and alkaline-earth carbonates and bicarbonates, such as for instance finely ground potassium carbonate, potassium bicarbonate, and magnesium and/or calcium carbonate.

The obtained protected amides may be converted into amides of formula (I) by cleaving the protective groups and any ester groups that might be present. A particularly preferred ester of this kind is the allyl ester, which is removable in highly selective conditions, for example through the transfer of the allyl group to a morpholine molecule, which, in the presence of Pd(0) as catalyst, acts as transferor of H and as nucleophile acceptor according to the procedure disclosed in J. Org. Chem., 54, 751 1989.

Amides of formula (I) wherein $R_2$ is a group of formula (III) can be prepared by reaction of primary and secondary amines of formula (I) with an isothioureide or the corresponding isothio-uronium salts of formula (III)

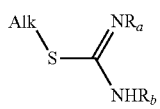
(IIIa)

wherein Alk is a $C_1$-$C_3$-alkyl and $R_a$ and $R_b$ are as defined above.

The prepararation of hydroxy-isothioureas of formula (IIIa), wherein Ra is OH and Rb is H, is described in Bernd Clement, Arch. Pharm. (Wheineim) 319, 968 (1986); other compounds of formula IIIa are known compounds or can be prepared by the conventional methods for alkylation in basic medium of the corresponding linear and/or cyclic thioureas and of thiosemicarbazides. The compounds of formula IIIa are isolated as isothio-uronium salts and may be reacted with the amines of formula Ie according to the method disclosed by Bodansky M. et al., J. Am. Chem. Soc., 86, 4452, 1964. Alternatively, an excess of a solvent such as ethyl acetate (AcOEt) is added to an aqueous solution or suspension of the isothio-uronium salt of formula IIIa and under vigorous stirring the salt is neutralized by adding the equivalent base solution (NaOH N, potassium carbonate N), to yield the corresponding isothioureide.

Amides of formula (Ia)

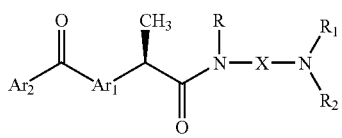
(Ia)

wherein $Ar_1$, $Ar_2$, X, R, $R_1$ and $R_2$ have the meanings disclosed above, can undergo reduction of the phenone carbonyl group to give a diastereoisomeric pair of R', S' alcohols optionally separated by fractioned crystallization and/or preparative chromatography to provide the individual diastereoisomers of formula (Ib):

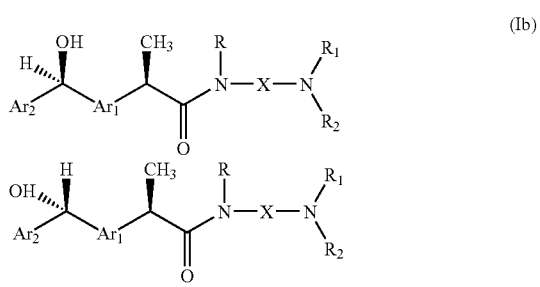
(Ib)

The convention has been adopted of indicating the absolute configuration S' to the most polar diastereoisomer.

Compounds of formula (I) may be converted into pharmaceutically acceptable salts through salification of the basic or acid groups which are present in their stricture, using respectively pharmaceutically acceptable acids or bases. Examples of salts with pharmaceutically acceptable bases are those with alkaline or alkaline-earth metals, preferably lithium, sodium and magnesium, or with organic bases, such as tromethamine, D-glucosamine, lysine, arginine.

The compounds of formula (I) are generally isolated in the form of their addition salts with both organic and inorganic pharmaceutically acceptable acids. Examples of these acids are: hydrochloric, nitric, sulfuric, phosphoric, formic, acetic, trifluoroacetic, propionic, maleic and succinic, malonic and methansulfonic, D and L-tartaric acids. The R enantiomers of the 2-arylpropionic acids of formula (Va):

(Va)

wherein Ar is as defined above, are weak inhibitors of cycloxygenases and are usually known compounds.

The acids of formula (Vb):

(Vb)

wherein φ and $Ar_b$ are as defined above, are obtained by alkylation with stannanes of a polysubstitute 2-phenyl-propionic acid bearing, in ortho or meta or para, a perfluorobutane-sulfonate group, as described herein below.

The compounds of formula (Vb) are disclosed in International patent application WO 01/58852. In particular, 2-[3'-isopropyl)phenyl]-propionic, 2-[3'-(α-methyl)benzyl)phenyl]-propionic and 2-[3'-(3-isopentyl)phenyl]-propionic acids, are among the preferred precursors of the amides of formula (I).

Each 2-arylpropionic acid can be prepared by total and stereospecific synthesis or by conversion of the racemate into one of the individual enantiomers after conversion into 2-aryl-2-propyl-ketenes, as disclosed by Larse R. D. et al., J. Am. Chem. Soc., 111, 7650, 1989, and by Myers A. G., ibidem, 119, 6496, 1997. Stereoselective syntheses of 2-arylpropionic acids are usually directed to the S enantiomers, but may be easily modified in order to obtain R enantiomers via a convenient choice of the chiral auxiliary agent. The use of arylalkylketones as reactants in the synthesis of α-arylalcanoic acids, is described for examplein B. M. Trost and J. H. Rigby, J. Org. Chem., 14, 2926, 1978; the arylation of Meldrum acids, is described in J. T. Piney and R. A. Rowe, Tetrah. Lett., 21, 965, 1980; the use of tartaric acid as chiral auxiliary agent, in G. Castaldi et al., J. Org. Chem., 52, 3019, 1987; the use of α-hydroxyesters as chiral reactants is reported in R. D. Larsen et al., J. Am. Chem. Soc., 111, 7650, 1989 and U.S. Pat. No. 4,940,813 and the references cited therein.

A process for the preparation of 2-(2-OH-phenyl)-propionic acids and their esters is disclosed in Italian patent No. 1,283,649. A tested and efficient method for the preparation of the R enantiomer of the (R,S)-2-(5-benzoyl-2-acetoxy)-propionic acid and of the acids of formula (Vb) disclosed above consists in the conversion of the chlorides of said prop-1-ketene acids by reaction with a tertiary amine, such as dimethyl-ethyl-amine, followed by the reaction of the ketene with R(-)-pantolactone, which yields the esters of R-enantiomers of said acids with R-dihydro-3-hydroxy-4,4-dimethyl-2(3H)-furan-2-one. The subsequent saponification of the ester with LiOH yields the corresponding free acid.

A general procedure for the preparation of R(-)-2-arylpropionic acids of formula (Vb) includes the reaction of hydroxyarylketones of formula (Vc) mono or polysubstituted with a perfluorobutanesulfonylfluoride to yield perfluorobutanesufonic esters of formula (Vd) where n is an integer from 1 to 9.

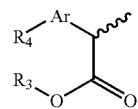
(Vc)

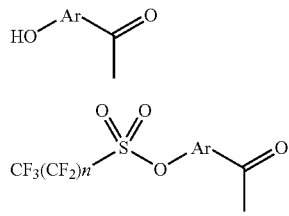
(Vd)

The compounds of formula (Vd) are subjected to Willoerodt re-arrangement to obtain, after esterification and methylation on the alpha carbon, arylpropionic derivates of formula (Ve) where n is an integer from 1 to 9 and $R_3$ represents a $C_1$-$C_4$ alkyl or a $C_2$-$C_4$ alkenyl.

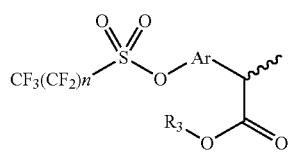
(Ve)

The compounds of formula (Ve) are reacted with the appropriate tributylstannane of formula $Bu_3SnR_5$ where $R_5$ is a linear or branched $C_1$-$C_6$ alkyl, a linear or branched $C_2$-$C_6$ alkenyl or a linear or branched $C_2$-$C_6$ alkynyl, non-substituted or substituted with an aryl group, to obtain the corresponding (R,S)-2-arylpropionates of formula (Vf).

(Vf)

The alkenyl or alkynyl groups can be hydrogenated in catalytic hydrogenation conditions to obtain the corresponding saturated alkyl groups. The compounds of formula (Vf) are submitted to the de-racemization process as disclosed above of conversion of the corresponding acid chlorides into ketenes which, by reaction with R(-)-pantonolactone and subsequent hydrolysis, are converted into pure R enantiomers.

The amines of formula (VI) are known products, mostly commercially available or can be prepared by known methods. The synthesis of 4-dialkylamino-2-butynyl-amine and, from this, of cis- and trans-4-dialkylamino-2-butenylamine is reported in R. Dalhome et al., J. Med. Chem., 9, 843, 1966 and T. Singh et al. ibidem, 12, 368, 1969, respectively.

α-Amino acids with an amino group of formula —$NR_1'R_2'$ bound to the terminal carbon atom are prepared by known methods starting from ω-hydroxy-α-amino acids, the carboxy and amino groups of which have been conveniently protected. The alcoholic group is transformed into a bromide through reaction with triphenylphosphine and $CBr_4$ (R G Weiss et al., J. Org. Chem. 36, 403, 1971 and M. Kang., ibidem, 64, 5528, 1966) followed by reaction of the halide thus obtained with at least 2M excess of the desired amine (i.e. dimethylamine, piperidine). Commercially available substrates for this purpose are serine and homoserine: superior homologs are obtained starting from commercially available dicarboxylic α-amino-acids protected at $C_1$ and at the amino group, the free carboxy group of which is selectively reduced to alcohol by reduction in THF at room temperature with an excess of diborane.

The present invention provides compounds of formula (I), which are R enantiomers of 2-arylpropionamides, for use as medicaments.

The compounds of the invention of formula (I) were evaluated "in vitro" for their ability to inhibit chemotaxis of polymorphonucleate leukocytes (hereinafter referred to as PMNs) and monocytes, induced by the fractions of the complement C5a and C5a-desArg. For this purpose, to isolate the PMNs from heparinized human blood, taken from healthy adult volunteers, mononucleates were removed by means of sedimentation on dextrane (according to the procedure disclosed by W. J. Ming et al., J. Immunol., 138, 1469, 1987) and red blood cells by a hypotonic solution. The cell vitality was calculated by exclusion with Trypan blue, whilst the ratio of PMNs was estimated on the cytocentrifugate after staining with Diff Quick.

The fractions hr-C5a and hrC5a-desArg (Sigma) were used as stimulating agents in chemotaxis experiments, obtaining practically identical results.

Lyophilized C5a was dissolved in a volume of HBSS containing 0.2% BSA so as to obtain a stock solution having a concentration of $10^{-5}$ M, to be diluted in HBSS to a concentration of $10^{-9}$ M, for the chemotaxis assays.

In the chemotaxis experiments, the PMNs were incubated with the compounds of the invention of formula (I) for 15' at 37° C. in an atmosphere containing 5% $CO_2$.

The chemotactic activity of the C5a was evaluated on human circulating polymorphonucleates (PMNs) resuspended in HBSS at a concentration of $1.5 \times 10^6$ PMNs per ml.

During the chemotaxis assay (according to W. Falket et al. J. Immunol. Methods, 33, 239, 1980) PVP-free filters with a porosity of 5 mcm and microchambers suitable for carrying out the test were used.

The compounds of the invention in formula (I) were evaluated at a concentration ranging between $10^{-6}$ and $10^{-10}$ M; for this purpose they were added, at the same concentration, both to the lower pores and the upper pores of the microchamber. The wells in the lower part contain the solution of C5a or the simple carrier, those in the upper part contain the suspension in PMNs.

Inhibition of C5a-induced chemotactic activity by the individual compounds of the invention of formula (I) was evaluated by incubating the microchamber for the chemotaxis for 60 min at 37° C. in an atmosphere containing 5% CO2.

Evaluation of the ability of the compounds of the invention of formula (I) to inhibit C5a-induced chemotaxis of human monocytes was carried out according to the method reported above (Van Damme J. et al., Eur. J. Immunol., 19, 2367, 1989). Inhibition of C5a-induced chemotactic activity by the individual compounds of the invention of formula (I) towards human monocytes was evaluated at a concentration ranging between $10^{-6}$ and $10^{-10}$ M by incubating the microchamber for the chemotaxis for 120 min. at 37° C. in an atmosphere containing 5% CO2.

The compounds of the invention were also evaluated in their ability to inhibit IL-8-induced chemotaxis of human PMNs. For this purpose, recombinant human interleukin-8 (rhIL-8, Pepro Tech) was used: the lyophilized protein was dissolved in HBSS (Hank's balanced salts solution) at the concentration of 100 mcg/mL and then diluted down to a concentration of 10 ng/mL in the chemotaxis experiments. R(−)-2-[(4'-isobutyl)phenyl]-propionyl methansulfonamide ($ED_{50}=10^{-9}$ M) described in WO 00/24710, was used as reference standard.

Results on inhibition of the chemotaxis induced by C5a and by IL-8 are listed in Table I. Results show that different structures of the amide group can lead to different selectivity in the compounds of the present invention.

A selected number of compounds are dual inhibitors, inhibiting chemotaxis induced both by C5a and by IL-8, others are selective inhibitors of the chemotaxis induced by C5a. For example, N-(1-methyl-pyrid-4-yl)amides, β-tropylamides, N-(H2N-alkyl)-amides of formula (I) are all selective inhibitors of C5a-induced chemotaxis of PMN and of monocytes in the concentration range between $10^{-6}$ and $10^{-8}$ M. All these compounds have shown poor activity as inhibitors of interleukin-8-induced chemotaxis in the same concentration range.

A selected number of compounds of the invention are able of inhibiting also interleukin 8-induced chemotaxis of PMN leukocytes and lymphocytes T, in addition to the C5a-induced chemotaxis of PMN leukocytes and monocytes in the concentration range between $10^{-6}$ and $10^{-8}$ M. More particularly, the compounds of formula (I) wherein R1 and R2 are different from hydrogen, exert both activities of inhibition of C5a-induced chemotaxis and IL-8-induced chemotaxis. Both activities are present in compounds wherein the distance between the terminal basic N and the amide N is between 2 and 4 C atoms, with an optimum for n=3. In this structural framework, it can be stated that the compounds of the invention exert the dual role of inhibitors of C5a-induced chemotaxis and IL-8-induced chemotaxis.

The compounds of formula (I), evaluated ex vivo in blood in toto according to the procedure disclosed by Patrignani et al., in J. Pharmacol. Exper. Ther., 271, 1705, 1994, were found to be totally ineffective as inhibitors of COX enzymes.

In almost all cases, the compounds of formula (I) do not interfere with the production of $PGE_2$ induced in murine macrophages by lipopolysaccharides stimulation (LPS, 1 μg/mL) at a concentration ranging between $10^{-5}$ and $10^{-7}$ M. Inhibition of the production of $PGE_2$ which may be recorded, is mostly at the limit of statistical significance, and more often is below 15-20% of the basal value.

In consideration of the experimental evidence discussed above and of the role of complement activation, through its fraction C5a, in pathologies such as psoriasis (R. J. Nicholoff et al., Am. J. Pathol., 138, 129, 1991), pemphigus and pemphigoid, rheumatoid arthritis (M. Selz et al., J. Clin. Invest., 87, 463, 1981), intestinal chronic inflammatory pathologies such as ulcerative colitis (Y. R. Mahida et al., Clin. Sci., 82, 273, 1992), acute respiratory distress syndrome, cystic fibrosis and idiopathic fibrosis (E. J. Miller, previously cited, and P. C. Carre et al., J. Clin. Invest., 88, 1882, 1991), Chronic Obstructive Pulmonary Disease (COPD), glomerilonephritis (T. Wada et al., J. Exp. Med., 180, 1135, 1994) as well as in the prevention and treatment of injury caused by ischemia and reperfusion, the compounds of the present invention are particularly useful to attain these therapeutic purposes.

The present invention thus provides the compounds of formula (I) for use in the treatment of psoriasis, pemphigus and pemphigoid, rheumatoid arthritis, intestinal chronic inflammatory patologies including ulcerative colitis, acute respiratory distress syndrome, systemic and pulmonary idiopathic fibrosis, cystic fibrosis, chronic obstructive pulmonary disease, glomerulonephritis and in the prevention and in the treatment of injury caused by ischemia and reperfusion.

The invention further provides the use of the compounds of formula (I) in the manufacture of medicaments for the treatment and prevention of said pathologies.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the amides of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the amide compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Liquid forms, including the injectable compositions described herebelow, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the amide derivative of formula I in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time.

The above described components for orally administered or injectable compositions are merely representative. Further materials as well as processing techniques and the like are set out in Part 8 of "Remington's Pharmaceutical Sciences Handbook", 18th Edition, 1990, Mack Publishing Company, Easton, Pa., which is incorporated herein by reference.

The compounds of this invention can also be administered in sustained release forms or from sustained release drug delivery systems. A description of representative sustained release materials can also be found in the incorporated materials in the Remington's Handbook as above.

The present invention shall be illustrated by means of the following examples which are not construed to be viewed as limiting the scope of the invention.

In the description of the compounds of the invention of formula (I), the convention has been adopted of indicating the absolute configurations of any additional chiral substituents, optionally present in the structure of said compounds, with prime signs (e.g., R', S', S" etc.).

Examples of abbreviations are: AcOH for acetic acid, AcOEt for ethyl acetate, BOC for N-tert-butoxycarbonyl-, DCC for dicyclohexylcarbodiimide, DCU for dicylohexylurea, DMF for dimethylformamide, EtOH for ethanol, Et2O for diethyl ether, HOBZ for 1-hydroxybenzothiazole, hr for hour, hrs for hours, MeOH for methanol, r.t. for room temperature, THF for tetrahydrofuran, Z for N-benzyloxycarbonyl.

Preparations:

Intermediate compounds, which are used in the Examples herebelow, have been prepared according to the following procedures.

1-amino,4-dimethylamino-butane

Dimethylamine hydrochloride (1.2 g; 12.5 mmol) and, 1 hr later, 4-bromobutylphtalimide (3.5 g; 12.4 mmol) are added to a suspension of $K_2CO_3$ (4.3 g; 31 mmol), in acetone (5 mL) at 25° C.; the suspension is then refluxed overnight. After cooling at r.t., the mixture is filtered and evaporated to dryness; silica gel flash chromatography of the residue oil (eluent $CHCl_3/CH_3OH$ 8:2) yields N-(4-dimethylamino-butyl)-phtalimide as a white solid (2.2 g; 8.94 mmol).

A solution of said compound in EtOH, treated with a 35% aqueous hydrazine (0.45 mL), is heated at reflux temperature until all the reagents are disappeared (~2 hrs), filtered and evaporated to dryness. Final crystallization from $CH_2Cl_2/CH_3OH$ (98:2) yields 0.85 g (7.32 mmol; 82% yield) of 1-amino, 4-dimethylamino-butane as a white solid.

$^1$H-NMR ($CDCl_3$): δ 7.75 (m, 2H); 7.65 (m, 2H); 2.72 (m, 2H); 2.35 (t, 2H, J=7 Hz); 2.23 (s, 6H); 1.75 (m, 2H); 1.56 (bs, 2H, $NH_2$); 1.48 (m, 2H).

1-amino,4-methylamino-butane

A lot of 1-amino, 4-methylamino-butane is obtained using methylamine instead of dimethylamine in the previous procedure.

1-(3-aminopropyl)-thiamorpholine

A solution of 3-BOC-aminopropyl bromide (3.07 g; 12.9 mmol) and thiamorpholine (2.6 mL; 25.8 mmol) in $CH_2Cl_2$ (25 mL) is heated at the reflux temperature for 24 h. The mixture is cooled at r.t., filtered, washed with water (2×50 mL), dried over $Na_2SO_4$ and evaporated to dryness in vacuum. Purification by flash chromatography on silica gel (eluent $CHCl_3/CH_3OH$ 9:1) yields 1-(3-BOC-aminopropyl)-thiamorpholine (3.1 g; 11.96 mmol), as a transparent oil.

Cleavage of the protective group is performed dissolving 1.4 g (5.4 mmol) of said compound in 3N aqueous HCl (6 mL) at r.t.; 18 hrs later, the solution, made alkaline by addition of aqueous 2N NaOH until to reach pH=8, is extracted with $CH_2Cl_2$ (2×10 mL). The combined extracts, dried over $Na_2SO_4$, are evaporated to dryness to give 1-(3-aminopropyl)-thiamorpholine as a transparent oil (0.63 g; 3.96 mmol).

$^1$H-NMR ($CDCl_3$): δ 7.75 (m, 2H); 7.65 (m, 2H); 2.72 (m, 2H); 2.35 (t, 2H, J=7 Hz); 2.23 (s, 6H); 1.75 (m, 2H); 1.56 (bs, 2H, $NH_2$); 1.48 (m, 2H).

1-(3-aminopropyl),4-methyl-piperazine(isolated as the hydrochloride salt)

$^1$H-NMR ($D_2O$): δ 3.75 (m, 7H); 3.45 (m, 3H); 3.15 (m, 2H); 3.05 (m, 4H); 2.20 (m, 2H) is obtained using 4-methyl-piperazine instead of thiamorpholine in the same procedure.

1-(3-aminopropyl)-piperidine $^1$H-NMR ($CDCl_3$): δ 2.85 (t, 2H, J=8 Hz); 2.45 (m, 6H); 1.90 (bs, 2H, $NH_2$); 1.8-1.62 (m, 6H); 1.55 (m, 2H) is obtained using piperidine instead of thiamorpholine in the same procedure.

1-BOC-propane-1,3-diamine

An aqueous solution (5 mL) of NaN3 (1.4 g; 21.5 mmol) and 2-3 drops of Aliquat 336 are added to a stirred solution of 3-BOC-amino-propyl bromide (5 g; 21.5 mmol) in toluene (10 mL); the mixture is heated at the reflux temperature for 4 hrs. After cooling at r.t., the organic phase is separated, dried over $Na_2SO_4$, and evaporated to dryness in vacuum to give 3-BOC-amino-propyl azide (3.75 g; 18.3 mmol) as a transparent oil (yield 85%).

A triphenylphosphine (4.8 g; 18.3 mmol) solution in THF (15 mL) is added dropwise to a stirred solution of the above azide in THF (30 mL)/H2O (0.3 mL; 18.3 mmol); the stirring is continued for 24 hrs at r.t. After removal of the solvents to dryness in vacuum, the residue is taken up with a few of EtOH to separate a white precipitate of triphenylphosphine oxide by stirring for 6 hrs at r.t. The final EtOH removal to dryness, at low pressure, gives 3.22 g (18 mmol) of 1-BOC-propane-1, 3-diamine as a pale yellow oil.

$^1$H-NMR (CDCl$_3$): δ 4.90 (bs, 1H, CONH); 3.25 (m, 2H), 2.85 (t, 2H, J=7 Hz); 1.75 (t, 2H, J=7 Hz); 1.60 (bs, 2H, NH$_2$); 1.55 (s, 9H).

3-(BOC-methylamino)-propylamine

It is obtained by use of 3-(BOC-methylamino)-propyl bromide in the previous procedure.

Methyl (S)-2-amino-3-dimethylamino-propionate

A 2M solution of dimethylamine in THF (2.5 mL) is added dropwise to a stirred solution of methyl (S) 2-BOC-amino-3-bromo-propionate (0.45 g; 1.42 mmol) (Weiss R. G. et al., J. Org. Chem, 36, 403, 1971; Kang M. et al., ibidem, 61, 5528, 1996) in anhydrous THF (10 mL) at 25° C. The mixture is stirred overnight at r.t. and evaporated to dryness in vacuum. The residue is partitioned between Et2O (30 mL) and aqueous 0.5 N NaOH (2×5 mL); the ethereal extracts are combined, washed with brine, dried over $Na_2SO_4$ and evaporated to dryness to obtain 0.34 g (1.22 mmol) of methyl (S)-2-amino-3-dimethylamino-propionate as a pale yellow oil.

$^1$H-NMR (CDCl$_3$): δ 7.45 (m, 5H); 5.73 (bs, 1H, CONH); 5.15 (s, 2H), 4.32 (m, 1H); 3.82 (s, 3H); 2.75 (m, 2H); 2.22 (s, 6H).

A stirred solution of said methyl ester (0.34 g; 1.22 mmol) in acetonitrile (12 mL) is treated with trimethylsilyl iodide (0.21 mL; 1.46 mmol) at r.t.; 3 hrs later, the mixture is quenched with MeOH (0.24 mL; 5.9 mmol) and evaporated in vacuum to dryness. The residue is taken up with Et2O (2×10 mL); the ethereal extracts are re-extracted with a 30% aqueous AcOH (2×5 mL), collected, made basic up to pH=8 and extracted with $CH_2Cl_2$ (2×10 mL). The dichloromethane extracts are combined, dried over $Na_2SO_4$, evaporated to dryness to yield 0.16 g (1.1 mmol) of methyl (S)2-amino-3-dimethylamino-propionate.

$^1$H-NMR (CDCl$_3$): δ 4.32 (m, 1H); 3.82 (s, 3H); 3.24 (bs, 2H, NH$_2$); 2.75 (m, 2H), 2.22 (s, 6H).

Methyl(S)-2-amino-5-(piperidin-1-yl)-pentanoate

Under stirring and with external cooling to maintain the reaction temperature between 20-25° C., 0.03 molar equivalents of 1 N B2H6 (diborane) solution in THF are added to a 0.01 M solution of (S)2-BOC-amino-1,5-pentadioic acid 1-hemi-methyl ester in THF (15 mL); 2 hrs later, the diborane excess is destroyed by cautious addition of water. After concentration to a small volume under vacuum, the solution is diluted with AcOEt (25 mL). The organic phase is washed with 5% aqueous NaHCO$_3$, brine and water to neutrality, dried over $Na_2SO_4$ and evaporated to dryness.

The crude residue of methyl (S)2-BOC-amino-5-hydroxy-pentanoate is treated with triphenylphosphine and CBr$_4$ to obtain a crude sample of methyl (S)2-BOC-amino-5-bromo-pentanoate.

Reaction of the latter compound with piperidine in THF provides methyl (S)2-BOC-amino-5-(piperidin-1-yl)-pentanoate that by treatment with a trifluoroacetic acid in dichloromethane, affords methyl (S)-2-amino-5-(piperidin-1-yl)-pentanoate bis-trifluoroacetate salt.

$^1$H-NMR (CDCl$_3$): δ 4.32 (m, 1H); 3.82 (s, 3H); 3.54 (m, 1H); 2.85 (t, 2H, J=7 Hz); 2.45 (m, 6H), δ 1.85 (bs, 2H, NH2); δ 1.75-1.6 (m, 6H), δ 1.5 (m, 2H).

5-BOC-ornithine-methyl ester hydrochloride

Maintaining the reaction temperature around 0-5° C. by external cooling, solid 2-Z,5-BOC-ornithine (1 g 2.7 mmol; commercial reagent) and, 15 min. later, methyl iodide (0.34 mL, 5.4 mmol) are added to a stirred suspension of finely powdered K$_2$CO$_3$ (0.38 g; 2.7 mmol) in dry DMF (20 mL). The mixture is stirred for an additional hr at 0-5° C. and at r.t. for 1 hr, then diluted with EtOAc (40 ml) and filtered. The clear solution is washed with water (40 ml) and brine (3×30 ml); dried over $Na_2SO_4$ and evaporated to dryness. Following purification by silica gel flash chromatography (eluent CHCl$_3$/CH$_3$OH 8:2) yields 2-Z,5-BOC-ornithine methyl ester (0.8 g; 2.1 mmol).

Hydrolytic cleavage of the Z protecting group (carried out according to the procedure of Meienhofer J. et. al, Tetrahedron. Lett., 3259, 1974) yields 5-BOC-ornithine methyl ester hydrochloride (0.73 g; 2.0 mmol) as a white solid.

$^1$H-NMR (CDCl$_3$): δ 9.25 (bs, 3H, NH$_3^+$); 5.40 (bs, 1H CONH); 4.40 (m, 1H); 3.8 (s, 3H); 3.0 (m, 2H); 1.8 (m, 4H); 1.4 (s, 9H).

Exo-8-methyl-8-aza-bicyclo[3,2,1]octan -3-amine(β-1H,5H-tropanamine)

A sample is prepared starting from tropinone according to the procedure of Burks J. E. et al., Org. Proc. Res. Dev., 1, 198, 1997.

4-(N,N-dimethylamino)aniline 4-nitroaniline (1.83 g; 13.24 mmol) is added portionwise to cooled (T=+4° C.) formic acid (3 mL; 66.2 mmol). Formaldehyde (37 wt. % solution in water; 2.72 mL; 29.13 mmol) is added and the resulting mixture refluxed for 24 h. After cooling at room temperature 6N HCl is added (2.2 mL) and the formed precipitate is filtered off. The filtrate is diluted with 1N NaOH (5 mL) and extracted with $CH_2Cl_2$ (3×20 mL); the organic collected extracts are dried over $Na_2SO_4$ and evaporated under vacuum to give a solid residue which, after treatment with a mixture of diisopropyl ether/acetone 1:1 and filtration, gives 4-nitro-N,N-dimethylaniline as a yellow powder (1.65 g; 9.93 mmol). Iron powder (2.145 g; 38.3 mmol) and 37% HCl (28 μl) are suspended in 96% ethyl alcohol (35 mL) and the mixture refluxed for 30'; at the end 4-nitro-N,N-dimethylaniline (0.64 g; 3.84 mmol) is added and the mixture left under reflux and stirring for 2 h. The hot mixture is filter over a Celite pad and, after cooling at room temperature, the filtrate is evaporated under vacuum. The oily residue is diluted with $CH_2Cl_2$ (25 mL) and washed with 1N NaOH (3×25 mL), dried over $Na_2SO_4$ and evaporated under vacuum to give 4-(N,N-dimethylamino)aniline as pale yellow oil (0.44 g; 3.26 mmol).

$^1$H-NMR ($CDCl_3$): δ 7.10 (d, 2H, J=8 Hz); 6.60 (d, 2H, J=8 Hz); 3.55 (bs, 2H, $NH_2$); 2.25 (s, 6H).

According the same procedure 4-(N,N-dimethylaminomethyl)aniline is prepared as pale yellow oil.

$^1$H-NMR ($CDCl_3$): δ 7.12 (d, 2H, J=8 Hz); 6.64 (d, 2H, J=8 Hz); 3.50 (bs, 2H, $NH_2$); 3.28 (s, 2H); 2.25 (s, 6H).

N,N-dimethylbutin-2-yl diamine

Propargyl bromide (1.3 mL, 17.4 mmol) is dissolved in DMF (30 mL) and potassium phtalimide (3.4 g; 18.4 mmol) is added. The mixture is refluxed for 5 h. After cooling at room temperature the mixture is diluted with diethyl ether, washed with water (3×50 mL), dried over $Na_2SO_4$ and evaporated under vacuum to give N-propargyl phtalimide as white solid (3.15 g; 17 mmol).

N-propargyl phtalimide (0.64 g; 3.4 mmol) is dissolved in 1,4-dioxane (20 mL), then dimethylamine (8.5 mL; 17 mmol), copper (I) chloride (0.35 g) and paraformaldehyde (1 g) are added. The solution is refluxed for 3 h. After cooling at room temperature the formed precipitate is filtered off and the filtrate is evaporated under vacuum to give a green oily residue that, after dissolution in $CH_2Cl_2$, is washed with sat. sol. $NaHCO_3$ (2×30 mL) and water (2×30 mL). The organic phase is dried over $Na_2SO_4$ and evaporated under vacuum. The crude product is purified by treatment with diethyl ether to give N-phtalimido-N',N'-dimethylbutin-2-yl-1,4-diamine as pale yellow solid (0.5 g; 2.05 mmol).

A suspension of N-phtalimido-N',N'-dimethylbutin-2-yl-1,4-diamine (0.5 g; 2.05 mmol) in ethyl alcohol (10 mL) is treated with hydrazine hydrate (98 μL; 2 mmol)) and the mixture is refluxed overnight. After cooling at room temperature the precipitate is filtered off and the filtrate is evaporated under vacuum; the crude residue is treated with acetone at room temperature to give, after removal of the formed precipitate, the pure product N,N-dimethylbutin-2-yl-1,4-diamine as red oil (0.2 g; 1.78 mmol).

$^1$H-NMR ($CDCl_3$): δ 3.52 (m, 2H); 3.27 (m, 2H); 2.35 (s, 6H); 1.90-1.65 (bs, 2H, $NH_2$).

2-(amineoxy)-N-methyl-N-(2-hydroxyethyl)]ethylamine a) (Z-amineoxy)-acetic acid

Maintaining the reaction temperature around 0-5° C. by external cooling, benzylchloroformate (1.41 mL, 10 mmol) and aqueous 4N NaOH (2.23 mL) are, dropwise and alternately, added to a solution in aqueous 2N NaOH:(5 mL) of 2.18 g (10 mmol) of carboxymethoxyamine hemihydrochloride [(commercial reagent) also named (aminoexy)acetic acidhydrochloride]. Stirring is continued for 15 min before removal of any organic impurities with $Et_2O$ (2×15 mL); then addition of crushed ice and acidification until pH=2 with 37% HCl yields a solid that is filtered, washed with cold water and dried under vacuum at T=40° C. to give 2.62 g (8.2 mmol) of (Z-amineoxy)-acetic acid.

b) 2-(Z-amineoxy)-N-methyl-N-(2-hydroxyethyl)acetamide

Thionyl chloride (0.78 mL, 9 mmol) is added to a stirred solution of (Z-amineoxy)-acetic acid (2.62 g, 8.2 mmol) in MeOH (10 mL). The mixture is maintained overnight at room temperature to give a crude sample of (Z-amineoxy)-acetyl chloride after the usual solvent evaporation under high-vacuum conditions. Without any further purification, a solution of said compound in $CH_2Cl_2$ (10 mL) is dropwise added at r.t. into a stirred solution of 2-methylaminoethanol (1.44 mL, 18 mmol) in $CH_2Cl_2$ (5 mL); 18 hrs later, the reaction mixture is diluted with aqueous 1N HCl (15 mL). The organic phase is separated; washed with water (2×15 mL), dried over $Na_2SO_4$ and evaporated to yield 2-(Z-amineoxy)-N-methyl-N-(2-hydroxyethyl)acetamide (2.64 g, 7 mmol) as a transparent oil.

c) 2-(Z-amineoxy)-N-methyl-N-(2-hydroxyethyl)ethylamine

The selective reduction with diborane of the 2-(Z-amineoxy)-N-methyl-N-(2-hydroxyethyl)acetamide, carried out according to the Brown procedure (J. Am. Chem. Soc. 86, 3566, 1964 and J. Org. Chem., 38, 912, 1973) yields 2.1 g (5.8 mmol) of 2-(Z-amineoxy)-N-methyl-N-(2-hydroxyethyl) ethylamine, as an oil.

d) 2-(aminoexy)-N-methyl-N-(2-hydroxyethyl)ethylamine

Benzyloxycarbonyl hydrogenolytic cleavage, carried out in the presence of ammonium formate according to Makowski procedure (Liebigs Ann. Chem., 1457, 1985) gives 2-(aminoexy)-N-methyl-N-(2-hydroxyethyl)ethylamine (1.06 g, 4.64 mmol) as a transparent oil.

$^1$H-NMR ($CDCl_3$): δ 5.28 (bs, 2H, $ONH_2$); 4.67 (t, 2H, J=7 Hz); 3.40 (m, 2H); 2.75 (t, 2H, J=7 Hz); $\overline{2.42}$ (t, 2H, J=7 Hz); 2.21 (s, 3H); 1.8 (bs, 1H, OH).

2-aryl-propionyl chlorides of formula V (general procedure)

A solution of 72.8 mmol of a 2-arylpropionic acid of formula V [for example, (R)-2-(4-isobutylphenyl)propionic acid, (R) (−).ibuprofen, 72.8 mmol] in thionyl chloride (37.5 mL) is refluxed for 3 hrs. The mixture is cooled at r.t.; the excess reagent is evaporated to dryness in vacuum; then, twice in succession, small amounts of anhydrous dioxane are added and evaporated to dryness under high vacuum conditions to fully eliminate any residual thionyl chloride. The final oily residue is used in the following reactions.

IR (film) $cm^{-1}$: 1800 (ClC=O)

(S)2-(4-isobutylphenyl)]-N-(3-dimethylaminopropyl)-propionamide hydrochloride

Using the previous procedure, (S)(+) ibuprofen (Fluka reagent) is converted into its propionyl chloride, whose treatment with 3-dimethylaminopropylamine, in the procedure of the example 1, allows to obtain a sample of (S)2-(4-isobutylphenyl)]-N-(3-dimethylaminopropyl)-propionamide hydrochloride m.p. 97-98° C., $[\alpha]_D$=+27(c=1; $CH_3OH$).

$^1$H-NMR ($D_2O$): δ 7.45-7.21 (m, 4H); 3.75 (q, 1H, $J_1$=7 Hz, $J_2$=7 Hz); 3.45-3.15 (m, 2H); 2.95 (t, 2H, J=8 Hz); 2.85 (s, 6H); 2.52 (d, 2H, J=7 Hz); 1.98 (m, 1H); 1.47 (d, 3H, J=7 Hz); 0.90 (d, 6H, J=7 Hz).

EXAMPLE 1

(R)2-(4-isobutylphenyl)-N-(3-dimethylaminopropyl) propionamide hydrochloride

With external cooling, keeping the reaction temperature below 40° C., a solution of (R)2-(4-isobutylphenyl)-propionyl chloride (16.35 g; 72.8 mmol) in $CH_2Cl_2$ (10 mL) is slowly added to a stirred solution of 3-dimethylaminopropylamine (19 mL; 152 mmol). After a night at r.t., the reaction mixture is diluted with water (100 mL), the organic phase is separated, washed with water (50 mL) and dried over $Na_2SO_4$. After solvent removal at low pressure, 20 g (68.8 mmol) of crude (R)2-(4-isobutylphenyl)-N-(3-dimethylaminopropyl)propionamide are obtained as a pale yellow oil.

A stirred solution of a portion of said amide (58 mmol) in isopropyl alcohol (200 mL) is treated with aqueous 37% HCl (6 mL), slowly added at r.t.; after 2 hrs, the reaction mixture is evaporated to dryness, at low pressure. The residual water is eliminated by azeotropic removal through the addition of small amounts of anhydrous isopropyl alcohol, in vacuum. Final crystallization from AcOEt (300 mL) separates a white powder that is filtered, washed with dry AcOEt and dried for 24 h under vacuum conditions at T=40° C. to obtain 18 g (55 mmol) of (R)2-(4-isobutylphenyl)-N-(3-dimethylaminopropyl) propionamide hydrochloride.

m.p. 95-98° C.,
$[\alpha]D=-26$ (c=1.6; $CH_3OH$).
$^1$H-NMR ($D_2O$): δ 7.5-7.2 (m, 4H); 3.75 (q, 1H, $J_1$=7 Hz, $J_2$=7 Hz); 3.45-3.15 (m, 2H); 3.05 (t, 2H, J=8 Hz); 2.80 (d, 6H, J=4.5 Hz); 2.55 (d, 2H, J=7 Hz); 1.95 (m, 1H); 1.45 (d, 3H, J=7 Hz); 0.93 (d, 6H, J=7 Hz).

EXAMPLE 2

Using 2-dimethylaminoethylamine and 4-dimethylaminobutylamine instead of 3-dimethylpropylamine in the procedure of the example 1, the following compounds are obtained:

(R)-2-(4-isobutylphenyl)-N-(2-dimethylaminoethyl) propionamide.HCl m.p. 90-93° C.; $[\alpha]_D=-16$ (c=1; $CH_3OH$).
$^1$H-NMR ($CDCl_3$): δ 12.25 (bs, 1H, $NH^+$); 7.82 (bs, 1H, CONH); 7.45 (d, 2H, J=8 Hz); 7.05 (d, 2H, J=8 Hz); 3.85 (m, 2H); 3.70 (m, 1H); 3.10 (m, 2H); 2,80 (s, 3H); 2.75 (s, 3H); 2.55 (d, 2H, J=7 Hz); 1.97 (m, 1H); 1.65 (d, 3H, J=7 Hz); 0.98 (d, 6H, J=7 Hz).

(R)2-(4-isobutylphenyl)-N-(4-dimethylaminobutyl) propionamide.HCl m.p. 95-97° C.; $[\alpha]_D=-16$ (c=0.52; $CH_3OH$).
$^1$H-NMR ($CDCl_3$): δ 7.25 (d, 2H, J=8 Hz); 7.10 (d, 2H, J=8 Hz); 6.18 (bs, 1H, CONH); 3.60 (q, 1H, $J_1$=7 Hz, $J_2$=7 Hz); 3.25-3.15 (m, 2H); 2.95 (m, 2H); 2.75 (s, 6H); 2.45 (d, 2H, J=7 Hz); 1.85 (m, 1H); 1.65 (m, 4H); 1.48 (d, 3H, J=7 Hz); 0.93 (d, 6H, J=7 Hz).

EXAMPLE 3

(R)2-(4-isobutylphenyl)-N-2-(N-morpholinyl ethyl) propionamide.HCl

Using 1-aminoethyl-morpholine in the procedure of the example 1, crude (R)2-(4-isobutylphenyl)-N-[2-(1-morpholinyl)ethyl]propionamide is obtained.

A solution of 4.2N acetyl chloride in absolute EtOH (3 mL) is added dropwise to a stirred solution of said amide (0.416 g, 1.3 mmol) in absolute EtOH (5 mL). The mixture is stirred for additional 2 hrs at r.t. before removal of solvents at low pressure. The residue is taken up with ethyl ether to separate 0.39 g (1.1 mmol) of (R)2-(4-isobutylphenyl)-N-[2-(1-morpholinyl)ethyl]propionamide hydrochloride as a white solid, that is filtered and washed with the same solvent.

m.p. 123-125° C.; $[\alpha]_D=-36.3$ (c=0.5; $CH_3OH$).
$^1$H-NMR ($CDCl_3$): δ 12.55 (bs, 1H, $NH^+$); 7.80 (bs, 1H, CONH); 7.45 (d, 2H, J=8 Hz); 7.05 (d, 2H, J=8 Hz); 4.25 (m, 2H); 3.95 (m, 1H); 3.70 (m, 4H); 3.41 (m, 1H); 3.05 (m, 3H); 2.75 (m, 2H); 2.45 (d, 2H, J=7 Hz); 1.97 (m, 1H); 1.65 (d, 3H, J=7 Hz)l 0.95 (d, 6H, J=7 Hz

EXAMPLE 4

The use in the procedure of the Example 3 of the following amines: 1-(3-aminopropyl)morpholine, 1-(3-aminopropyl)-4-thiomorpholine, 1-(2-aminoethyl)-piperazine-4-methyl, 1-(3-aminopropyl)-piperazine-4-methyl, 1-(3-aminopropyl) piperidine, and exo-8-methyl-8-aza-bicyclo[3,2,1]octan-3-amine instead of 1-(3-aminopropyl)morpholine gives:

(R)2-(4-isobutylphenyl)-N-3-(N-morpholinyl propyl) propionamide.HCl m.p. 90-93° C.
$[\alpha]_D=-22.6$ (c=0.5; $CH_3OH$).
$^1$H-NMR ($CDCl_3$): δ 12.55 (bs, 1H, $NH^+$); 7.80 (bs, 1H, CONH); 7.45 (d, 2H, J=8 Hz); 7.05 (d, 2H, J=8 Hz); 4.25 (m, 2H); 3.95 (m, 1H); 3.70 (m, 4H); 3.41 (m, 1H); 3.05 (m, 3H); 2.75 (m, 2H); 2.45 (d, 2H, J=7 Hz); 2.15 (m, 2H); 1.97 (m, 1H); 1.65 (d, 3H, J=7 Hz); 0.95 (d, 6H, J=7 Hz).

(R)2(4-isobutylphenyl)-N-3-(N-thiomorpholinyl propyl)propionamide HCl m.p. 70-73° C.; $[\alpha]_D=-23$ (c=0.5; $CH_3OH$).
$^1$H-NMR ($D_2O$): δ 8.15 (bs, 1H, CONH); 7.40 (m, 4H); 3.82 (q, 1H, J=7 Hz); 3.65 (m, 2H); 3.41 (m, 1H); 3.25 (m, 1H); 3.15-2.80 (m, 8H); 2.45 (d, 2H, J=7 Hz); 1.95 (m, 3H); 1.55 (d, 3H, J=7 Hz); 0.95 (d, 6H, J=7 Hz).

(R)2-(4-isobutylphenyl)-N-[2-(4-methyl-piperazin-1-yl)ethyl]propionamide hydrochloride m.p. above 240° C.; $[\alpha]_D=-33.7$ (c=0.5; $CH_3OH$).
$^1$H-NMR (DMSO-$d_6$): δ 7.15 (m, 4H); 4.45 (M, 1H); 4.13 (m, 2H); 3.02 (m, 3H); 2.75 (m, 4H); 2.38 (d, 2H, J=7 Hz); 1.85 (m, 1H); 1.30 (d, 3H, J=7 Hz); 0.81 (d, 6H, J=7 Hz).

(R)2-(4-isobutylphenyl)-N-[3-(4-methyl-piperazin-1-yl)propyl]propionamide bis-hydrochloride m.p. 216-220° C.; $[\alpha]_D=-20.5$ (c=0.5; $CH_3OH$).
$^1$H-NMR ($D_2O$): δ 7.25 (m, 4H); 3.75 (m, 1H); 3.55 (m, 8H); 3.25 (m, 2H); 3.15 (m, 1H); 3.00 (s, 3H); 2.48 (d, 2H, J=7 Hz); 1.95 (m, 3H); 1.45 (d, 3H, J=7 Hz); 0.90 (d, 6H, J=7 Hz).

(R)2-(4-isobutylphenyl)-N-[3-(1-piperidinyl)propyl] propionamide hydrochloride m.p. 76-80° C.;
$[\alpha]_D=-29$ (c=0.5; $CH_3OH$).
$^1$H-NMR ($CDCl_3$): δ 11.4 (bs, 1H, $NH^+$); 7.45 (d, 2H, J=8 Hz); 7.35 (bs, 1H, CONH); 7.05 (d, 2H, J=8 Hz); 3.85 (q, 1H, J=7 Hz); 3.45 (m, 4H); 2.75 (m, 2H); 2.52 (m, 4H); 2.25 (m, 2H); 2.05 (m, 2H); 1.97 (m, 3H); 1.60 (d, 3H, J=7 Hz); 0.97 (d, 6H, J=7 Hz).

(R)2-(4-isobutylphenyl)-N-(exo-8-methyl-8-aza-bicyclo[3.2.1]oct-3-yl)propionamide hydrochloride m.p. 72-75° C.; $[\alpha]_D=-3.3$ (c=0.5; $CH_3OH$).
$^1$H-NMR ($CDCl_3$): δ 7.15 (d, 2H, J=8 Hz); 7.05 (d, 2H, J=8 Hz); 6.15 (bs, 1H, CONH); 4.34 (m, 1H); 3.75 (m, 2H); 3.47 (q, 1H, J=7 Hz); 2.72 (s, 3H); 2.60-2.38 (m, 4H); 2.30-1.98 (m, 6H); 1.92 (m, 2H); 1.45 (d, 3H, J=7 Hz); 0.9 (d, 6H, J=7 Hz).

EXAMPLE 5

(R)2-(4-isobutylphenyl)-N-(3-aminopropyl)propionamide hydrochloride

A solution of 3-BOC-aminopropylamine (3.22 g; 18 mmol) in $CH_2Cl_2$ (10 mL) is added dropwise to a stirred suspension of (R)(−) ibuprofen (3 g; 17.5 mmol), DCC (3.8 g; 18 mmol) and HOBZ (2.8 g; 18 mmol) in $CH_2Cl_2$ (50 mL) at 25° C. The stirring is continued for 18 hrs at r.t.; after DCU removal by filtration, the reaction mixture is evaporated to dryness in vacuum. The residue oil is more times taken up with acetonitrile; finally the collected extracts are filtered, evaporated to dryness to give a crude sample of (R)2-(4-isobutylphenyl)-N-3-(BOC-aminopropyl)propionamide that is crystallized from hot MeOH (50 mL) to obtain 3.4 g (9.25 mmol,. 53% yield) of pure (R)2-(4-isobutylphenyl)-N-3-(BOC-aminopropyl)propionamide by cooling at T=+4° C. for 18 hrs A suspension of said compound in 10 mL of aqueous 3N HCl is stirred at r.t. for 48 hrs to give (R)2-(4-isobutylphenyl)-N-3-(aminopropyl)propionamide hydrochloride (1.9 g; 6.3 mmol);

m.p. 160-163° C.;
$[\alpha]_D = -31$ (c=0.5; $CH_3OH$).
$^1$H-NMR ($CDCl_3$): δ 8.2 (bs, 1H, $NH_3^+$); 7.18 (d, 2H, J=8 Hz); 7.05 (d, 2H, J=8 Hz); 6.83 (bs, 1H, CONH); 3.65 (q, 1H, J=7 Hz); 3.30 (m, 2H); 3.00 (m, 2H); 2.40 ($\overline{d}$, 2H, J=7 Hz); 1.95-1.74 (m, 3H); 1.45 (d, 3H, J=7 Hz); 0.92 (d, 6H, J=7 Hz).

EXAMPLE 6

(R)2-(4-isobutylphenyl)-N-(1-methyl-piperidin-4-yl) propionamide hydrochloride

Ammonium formate (15.4 g; 240 mmol) and 10% Pd/C (3.14 g; 29 mmol) are added to a solution of 1-methyl-4-piperidone (3.26 mL; 26.5 mmol) in aqueous methanol (80 mL, $CH_3OH/H_2O$ 9:1); the mixture is stirred for 24 h. at r.t.;. catalyst removal by filtration over Celite and solvent evaporation to dryness at low pressure give a pale yellow residue of 1-methyl-4-aminopiperidine. Dropwise addition of 37% HCl (4.6 mL) to a stirred solution of said amine in EtOH (50 mL) separates a white precipitate of 1-methyl-4-aminopiperidine hydrochloride that is filteted 18 hrs later, after cooling for 18 hrs at T=+4° C. Finally, an aqueous solution of the hydrochloride treated with an excess of 0.1 N NaOH (≈10 mL) is extracted with $CH_2Cl_2$ (3×10 mL). After the usual work-up, solvent evaporation to dryness yields pure 1-methyl-4-aminopiperidine (1.4 g; 12.4 mmol).

$^1$H-NMR ($CDCl_3$): δ 2.85 (m, 2H); 2.58 (m, 1H); 2.25 (s, 3H); 2.01 (m, 2H); 1.85 (m, 2H); 1.63 (bs, 2H, $\underline{NH_2}$); 1.47 (m, 2H).

At room temperature, a solution of (R)2-(4-isobutylphenyl)-propionyl chloride (1.12 g; 5 mmol) in $CH_2Cl_2$ (20 mL) is slowly added dropwise to a solution of 1-methyl-4-aminopiperidine (1.1 g; 10 mmol) in $CH_2Cl_2$ (10 mL). After 3 hrs., the reaction mixture is diluted again with $CH_2Cl_2$ (10 mL), washed with 1 N HCl (25 mL) and with brine, dried over $Na_2SO_4$ to give after solvent removal to dryness (R)2-(4-isobutylphenyl)-N-(1-methyl-piperidin-4-yl)propionamide hydrochloride as a glass solid (1.2 g; 3.5 mmol).

$[\alpha]_D = -11$ (c=0.5; $CH_3OH$).
$^1$H-NMR ($D_2O$): δ 7.28 (m, 5H); 3.95 (m, 1H); 3.75 (q, 1H, J=7 Hz); 3.54 (m, 2H); 3.15 (m, 2H); 2.90 (s, 3H); 2.53 (d, 2H, J=7 Hz); 2.28-2.05 (m, 2H); 1.95-1.65 (m, 4H); 1.45 (d, 3H, J=7 Hz); 0.95 (d, 6H, J=7 Hz).

EXAMPLE 7

(R),(S)2-(4-isobutylphenyl)-N-(1-carboxy-2-dimethylamino-ethyl)propionamide sodium salt A solution of (S)methyl 3-dimethylamino-2-amino-propanoate (0.16 g; 1.1 mmol) in $CH_2Cl_2$ (2 mL) is added dropwise to a stirred suspension of (R)(−)ibuprofen (0.23 g; 1.1 mmol), DCC (0.23 g; 1.1 mmol) and HOBZ (0.17 g; 1.1 mmol) in $CH_2Cl_2$ (5 mL) at room temperature. The stirring is continued for 18 hrs at r.t.; after DCU removal by filtration, the reaction mixture is evaporated to dryness in vacuum. The residue is more times taken up with acetonitrile; then, the collected extracts are filtered and evaporated to dryness in vacuum. Following purification by flash chromatography on silica gel (eluent $CH_2Cl_2/CH_3OH$ 95:5) yields 0.3 g (0.88 mmol) of methyl (S),(R)3-dimethylamino-2-[2-(4-isobutylphenyl)propionyl]amino-propanoate (80% yield) as a transparent oil.

A stirred solution of said ester (0.3 g; 0.88 mmol) in dioxane (2 mL) is treated with a stechiometrical amount of aqueous N NaOH (0.88 mL) and maintained for 18 hrs. at r.t., before dilution with cooled water (20 mL). The frozen solution is lyophilized to yield 0.307 g (0.88 mmol) of (R),(S)2-(4-isobutylphenyl)-N-(1-carboxy-2-dimethylamino-ethyl) propionamide sodium salt, as a white solid m.p. above 240° C.;
$[\alpha]_D = -25$ (c=0.5; $CH_3OH$)
$^1$H-NMR ($CDCl_3$): δ 7.35 (m, 4H); 6.25 (bs, 1H, CONH); 4.72 (m, 1H); 3.60 (m, 1H); 2.51 (d, 2H, J=7 Hz); 2.30 (d, $\overline{2H}$, J=7 Hz); 2.22 (m, 6H); 1.55 (d, 3H, J=7 Hz); 0.95 (d, 6H, J=7 Hz).

EXAMPLE 8

(R),(S)2-(4-isobutylphenyl)-N-(1-carboxy-2-piperidin-1-yl-butyl)propionamide sodium salt; and (R),(S)2-(4-isobutylphenyl)-N-(1-ethoxycarbonyl-2-piperidin-1-yl-butyl)propionamide are obtained using (S)methyl-5-(piperidin-1-yl)-2-aminopentanoate in the procedure of the example 7 instead of (S)methyl3-dimethylamino-2-amino-propanoate.

EXAMPLE 9

R-2-[(4'-isobultylphenyl]-N-[2-(dimethylaminoethyl) aminocarbonylmethyl]-propionamide hydrochloride HOBZ (0.607 g; 4.49 mmol) is added to a stirred solution of (R)(−)ibuprofen (1.01 g; 4.9 mmol) in DMF (4 mL) at T=0° C. and left under stirring for 30 min. Then a mixture of N-(3-dimethylaminopropyl)glycinamide hydrochloride (0.64 g; 4.47 mmol) in DMF (8 mL) and triethylamine (0.6 mL; 4.45 mmol) is added and N,N-dicyclohexylcarbodiimide (1 g; 4.85 mmol), in small portions, is also added. The mixture is stirred for 2 hrs at T=0° C. and then for 18 hrs at r.t. After DCU filtration most of DMF is then removed by distillation at low pressure. The residue is taken up with water and extracted with $Et_2O$ (3×25 mL); the organic extracts are combined, dried over $Na_2SO_4$, and evaporated a low pressure to yield a transparent oil (1 g; 3.43 mmol). Then a solution of this compound in dioxane (3.5 mL) is treated with 1N NaOH (3.5 mL), stirred for 24 hrs at r t., diluted with water (10 mL) and then acidified with 2N HCl, and extracted with $CH_2Cl_2$ (3×10 mL). Then, the organic extracts are combined, dried over $Na_2SO_4$, evaporated at low pressure to yield R-2-[(4'-isobutyl)phenyl]-N-[2-(dimethylaminoethyl)aminocarbonylmethyl]-propionamide hydrochloride (0.68 g; 2.04 mmol), as a pale yellow oil.

$[\alpha]_D=-25$ (c=0.5; $CH_3OH$).

$^1$H-NMR ($CDCl_3$): δ 7.24 (m, 2H); 7.10 (m, 2H); 6.10 (bs, 1H, CONH); 3.55 (m, 1H); 3.30 (m, 2H); 2.45 (d, 2H, J=7 Hz); 2.35 (m, 2H); 2.18 (s, 6H); 1.85 (m, 1H); 1.52 (d, 3H, J=7 Hz); 0.90 (d, 6H, J=7 Hz).

EXAMPLE 10

(R)-2-[2-(2,6-dichlorophenylamino)-phenyl]-N-3-(dimethylaminopropyl)propionamide A suspension of (R)2-[2-(2,6-dichlorophenylamino)]phenyl]propionic acid (0.15 g; 0.48 mmol), DCC (0.173 g; 0.84 mmol) and HOBZ (0.075 g; 0.56 mmol) in $CH_2Cl_2$ (6 m L) is stirred for 4 hrs at r.t.; then, a solution of 3-(dimethylamino) propylamine (0.06 ml; 0.48 mmol) in $CH_2Cl_2$ (5 mL) is added dropwise. The stirring is continued for 18 hrs at r.t., then the separated DCU is filtered and the solvent removed at low pressure. The residue is taken up with acetonitrile twice, the extracts are combined, filtered to totally eliminate DCU, and evaporated at low pressure. Purification by flash chromatography (eluent $CH_2Cl_2/CH_3OH$ 95:5) yields (R)2-[2-(2,6-dichlorophenylamino)-phenyl]-N-3-(dimethylaminopropyl) propionamide (0.141 g; 0.36 mmol; 75% yield), as a transparent oil.

$[\alpha]_D=-30$ (c=1; $CH_3OH$).

$^1$H-NMR ($D_2O$): δ 7.38 (m, 4H); 7.15 (m, 1H); 7.05 (m, 1H); 6.60 (m, 1H+CONH); 4.25 (dd, 2H, $J_1$=7 Hz, $J_2$=3 Hz); 3.30 (m, 2H); 2.35 (m, 2H); 2.10 (s, 6H); 1.65 (m, 2H); 1.65 (d, 3H, J=7 Hz).

EXAMPLE 11

The following amides are obtained using (R),(R',S')-2-[3-(α-hydroxybenzyl)phenyl]propionic acid, 2-[3'-(α-hydroxyethyl)phenyl]propionic acid and (R),(R',S')2-[3'-(α-hydroxy, α-methylbenzyl)phenyl]propionic acid as starting material instead of (R)2-[2-(2,6-dichlorophenylamino)]phenyl]propionic acid in the procedure of example 10.

(R),(R',S')2-[3-(α-hydroxybenzyl)phenyl]-N-3-(dimethylaminopropyl)propionamide as a colourless oil $[\alpha]_D=-24$ (c=1; CH3OH).

$^1$H-NMR ($CDCl_3$): δ 7.41-7.3 (m, 3H); 7.31-7.14 (m, 6H); 5.75 (s, 1H); 4.02 (bs, 1H, OH) 3.31 (m, 2H); 2.38 (t, 2H, J=8 Hz); 2.15 (s, 6H); 1.75 (m, 2H); 3.68 (q, 1H, J=7 Hz); 1.4 (d, 3H, J=7 Hz).

(R),(R',S')2-[3'-(α-hydroxy, α-methylbenzyl)phenyl]-N-3-(dimethylaminopropyl)propionamide as a colourless oil $[\alpha]_D=-28$ (c=1; $CH_3OH$).

$^1$H-NMR ($CDCl_3$): δ 7.41-7.3 (m, 3H); 7.31-7.14 (m, 6H); 4.02 (bs, 1H, OH) 3.31 (m, 2H); 2.38 (t, 2H, J=8 Hz); 2.15 (s, 6H); 1.75 (m, 2H); 3.68 (q, 1H, J=7 Hz); 1.4 (d, 3H, J=7 Hz).

(R),(R',S')2-3-(α-hydroxyethyl)phenyl]-(3-dimethylaminopropyl)propionamide $^1$H-NMR (DMSO-$d_6$): δ 8.12 (bs, 1H, CONH); 7.31 (s, 1H); 7.25-7.10 (m, 3H); 5.1 (bs, 1H, OH); 4.7 (m, 1H); 3.62 (m, 1H); 3.10 (m, 2H); 2.91 (m, 2H); 3.65 (s, 6H); 1.73 (m, 2H); 1.30 (m, 6H)

EXAMPLE 12

(R),(R',S')2-[3'-(α-methylbenzyl)phenyl]-N-3-(dimethylaminopropyl)propionamide as a pale yellow oil (1.2 g, 3.52 mmol)

$[\alpha]_D=-30$ (c=1; $CH_3OH$).

$^1$H-NMR ($CDCl_3$): δ 7.38-7.13 (m, 9H); 6.60 (bs, 1H, CONH) 4.20 (m, 1H); 3.78 (m, 1H); 3.27 (m, 2H); 2.30 (m, 2H); 2.12 (s, 6H); 1.72 (d, 3H, J=7 Hz); 1.65 (m, 2H); 1.55 (d, 3H, J=7 Hz) is prepared using the (R),(R',S')2-[3-(α-methylbenzyl)phenyl]propionyl chloride in the procedure of the example 1 instead of the (R)2-(4-isobutylphenyl)-propionyl chloride.

The alternative use of (R)2-(3-isopropylphenyl)propionyl chloride, (R)2-(3-isobutylphenyl), (R)2-[3-(styren-1-yl)phenyl]propionyl chloride, (R)2-[3'-(pent-3-yl)phenyl]propionyl chloride in the procedure of the example 1 gives:

(R)2-(3-isopropylphenyl)-N-3-(dimethylaminopropyl)propionamide $^1$H-NMR ($CDCl_3$): δ 7.21-7.13 (m, 4H); 6.95 (bs, 1H, CONH) 3.53 (m, 1H); 3.30 (m, 2H); 2.90 (m, 1H); 2.37 (m, 2H); 2.15 (s, 6H); 1.65 (d, 3H, J=7 Hz); 1.23 (d, 3H, J=7 Hz).

(R)2-(3-isobutylphenyl)-N-3-(dimethylaminopropyl)propionamide $[\alpha]_D=-30$ (c=1; $CH_3OH$).
$^1$H-NMR ($CDCl_3$): δ 7.21-7.13 (m, 4H); 6.85 (bs, 1H, CONH) 3.53 (m, 1H); 3.25 (m, 2H); 2.48 (d, 2H, J=7 Hz); 2.30 (t, 2H, J=7 Hz); 209 (s, 6H); 1.9 (m, 1H); 1.55 (m, 2H); 1.45 (d, 3H, J=7 Hz); 0.95 (d, 3H, J=7 Hz).

(R)2-[3-(styren-1-yl)-phenyl]-N-3-(dimethylaminopropyl)propionamide $[\alpha]_D=-31$ (c=1; $CH_3OH$).
hu 1H-NMR ($CDCl_3$): δ 7.8-7.13 (m, 9H); 6.95 (bs, 1H, CONH) 5.0 (s, 2H); 3.53 (m, 1H); 3.30 (m, 2H); 2.37 (m, 2H); 2.15 (s, 6H).

(R)2-[3'-(pent-3-yl)phenyl]-N-3-(dimethylaminopropyl)propionamide $[\alpha]_D=-28$ (c=1; $CH_3OH$).
$^1$H-NMR ($CDCl_3$): δ 7.25 (m, 3H); 7.12 (m, 1H); 7.08 (bs, 1H, CONH) 3.65 (m, 1H); 3.5-3.13 (m, 2H); 2.75 (m, 2H); 2.55 (s, 6H); 2.35 (m, 1H); 1.95 (m, 2H); 1.70 (m, 2H); 1.58 (m, 2H); 1.50 (d, 3H, J=7 Hz); 0.76 (t, 6H, J=7 Hz).

(R)-2-[(3-benzoyl)phenyl]-N-(3-diethylaminopropyl)propionamide $[\alpha]_D=-11.5$ (c=3;$CH_3OH$)
$^1$H-NMR ($CDCl_3$): δ 7.8 (m, 3H); 7.70-7.55 (m, 3H); 7.50-7.28 (m, 3H); 7.25 (bs, 1H, CONH); 3.75 (m, 1H); 3.50-3.20

(m, 2H); 3.3.15-2.80 (m, 6H); 2.05 (m, 2H); 1.65 (d, 3H, J=7 Hz); 1.70-1.53 (m, 3H); 1.50-1.45 (m, 3H).

(R)-2-[(3-benzoyl)phenyl]-N-(3-dimethylaminopropyl)propionamide $[\alpha]_D$=−20 (c=1; $CH_3OH$)
$^1$H-NMR ($CDCl_3$): δ 7.88-7.78 (m, 3H); 7.75-7.58 (m, 3H); 7.55-7.46 (m, 3H); 7.25 (bs, 1H, CONH); 3.62 (m, 1H); 3.28 (m, 2H); 2.35 (m, 2H); 2.12 (s, 6H); 1.68-1.53 (m, 5H).

EXAMPLE 13

(R)2-(4-isobutylphenyl)-N-3(guanidinylpropyl)propionamide hydrochloride (R)2-[(4-isobutylphenyl)-N-3-(aminopropyl)propionamide hydrochloride of example 5 is converted into the free amine and treated with isothiouronium chloride according to the procedure of Bodanszky M. et al., (J. Am. Chem. Soc., 86, 4452, 1964) to obtain (R)2-(4-isobutylphenyl)-N-3(guanidinylpropyl)propionamide hydrochloride
m.p. 142-146° C.; $[\alpha]_D$=−24 (c=1; $CH_3OH$).
$^1$H-NMR ($D_2O$): δ 7.2 (d, 2H, J=8 Hz); 7.1 (d, 2H, J=8 Hz); 6.8 (bs, 1H, CONH); 3.6 (q, 1H, J=7 Hz); 3.55 (m, 2H); 2.95 (m, 2H); 2.4 (d, 2H, J=7 Hz); 2.0-1.8 (m, 3H); 1.5 (d, 3H, J=7 Hz); 0.9 (d, 6H, J=7 Hz).

Alternative use in the same procedure of the N-hydroxycarbamidothioic acid methylester hydrochloride salt and of the N-amino-carbamidothioic acid methylester gives:

(R)2-(4-isobutylphenyl)-N-[3-(hydroxyguanidinyl)propyl]propionamide.HCl (R)2-(4-isobutylphenyl)-N-[3-(aminoguanidinyl)propyl]propionamide.HCl

EXAMPLE 14

(R)2-(4-isobutylphenyl)-N-[3-(imidazolin-2-yl)aminopropyl]propionamide

The (R)2-[(4-isobutylphenyl)-N-3-(aminopropyl)propionamide hydrochloride (see example 5) is converted in the free amine and treated with 2-methylthio-2-imidazoline iodohydrate (commercial reactant) according to the above cited Bodanszky procedure (J. Am. Chem. Soc., 86, 4452, 1964) to give (R)2-(4'-isobutylphenyl)-N-[3-(imidazolin-2-yl)aminopropyl]propionamide
m.p. 155-168° C.; $[\alpha]_D$=−15 (c=1; $CH_3OH$).
$^1$H-NMR ($D_2O$): δ 7.2 (d, 2H, J=8 Hz); 7.1 (d, 2H, J=8 Hz); 6.8 (bs, 1H, CONH); 3.6 (q, 1H, J=7 Hz); 3.55 (m, 2H); 3.40 (s, 4H); 2.90 (m, 2H); 2.35 (d, 2H, J=7 Hz); 2.0-1.8 (m, 3H); 1.55 (d, 3H, J=7 Hz); 1.0 (d, 6H, J=7 Hz).

The use of 2-methylthio-tetrahydropyrimidine in the above procedure yields: (R)2-(4-isobutylphenyl)-N-[3-(tetrahydropyrimidine-2-yl)aminopropyl]propionamide.
$^1$H-NMR ($D_2O$): δ 7.2 (d, 2H, J=8 Hz); 7.1 (d, 2H, J=8 Hz); 6.8 (bs, 1H, CONH); 3.6 (q, 1H, J=7 Hz); 3.55 (m, 2H); 3.40 (s, 4H); 2.90 (m, 2H); 2.35 (d, 2H, J=7 Hz); 2.0-1.8 (m, 5H); 1.55 (d, 3H, J=7 Hz); 1.0 (d, 6H, J=7 Hz).

EXAMPLE 15

(R),(S')2-(4-isobutylphenyl)-N-[(1-carboxy-4-amino)butyl]propionamide

A solution of (R)2-(4-isobutylphenyl)propionyl chloride (0.54 g; 2.42 mmol) in $CH_2Cl_2$ (10 mL) is slowly added dropwise to a suspension of 5-BOC-ornithine methyl ester hydrochloride (0.69 g; 2.42 mmol) and triethylamine (0.68 mL; 4.84 mmol) in $CH_2Cl_2$ at 25° C. The mixture is kept under stirring overnight at r.t., then diluted with water (10 mL). The organic phase is separated and washed with a saturated solution of $NaHCO_3$ (10 mL), dried over $Na_2SO_4$, and evaporated to obtain a crude product, which is purified by flash chromatography (eluent $CHCl_3/CH_3OH$ 9:1) to yield (R),(S)2-(4-isobutylphenyl)propionyl-(5-BOC)ornithine methyl ester as a transparent oil (0.6 g; 1.4 mmol). Treatment of said compound with HCl 3N (8 mL) for 18 h at r.t. followed by solvent evaporation yields (R),(S')2-(4-isobutylphenyl)-N-[(1-methoxycarbonyl-4-amino)butyl]propionamide hydrochloride (0.41 g, 1.25 mmol).

To a solution of said hydrochloride in dioxane 4N NaOH (0.625 mL; 2.5 mmol) is added at r.t. the mixture is stirred overnight and evaporated to dryness at low pressure. The residue is taken up with EtOAc (15 mL); the organic phase is washed with a saturated NaCl solution (2×15 mL) and dried over $Na_2SO_4$. AcOEt evaporation yields (R),(S')2-(4-isobutylphenyl)-N-[(1-carboxy-4-amino)butyl]propionamide as a white solid,
m.p. above 240° C.;
$[\alpha]_D$=−29 (c=0.5; $CH_3OH$).
$^1$H-NMR (DMSO-$d_6$): δ 7.3 (d, 2H); δ 7.1 (d, 2H); 6.25 (bs, 1H, CONH); 4.20 (m, 1H); 3.70 (m, 1H); 3.50 (m, 2H); 2.5 (d, 2H); 1.9 (m, 1H); 1.8 (m, 4H); 1.6 (d, 3H); 0.95 (d, 6H, J=7 Hz).

(R),(S')2-(4'-isobutylphenyl)-N-(1-carboxy-5-aminopentyl)propionamide hydrochloride Prepared using the corresponding (L)-lysine derivative instead of the ornithine derivative.
$[\alpha]_D$=−28.3 (c=1; $CH_3OH$)
$^1$H-NMR (DMSO-$d_6$): δ 12.62 (bs, 1H, COOH); 8.25 (d, 1H, CONH, J=8 Hz); 7.75 (bs, 3H, $NH_3^+$); 7.25 (d, 2H, J=8 Hz); 7.06 (d, 2H, J=8 Hz); 4.15 (m, 1H); 3.70 (m, 1H); 2.63 (m, 2H); 2.38 (d, 2H, J=7 Hz); 1.92-2.78 (m, 1H); 1.70-1.38 (m, 4H); 1.35 (d, 3H, J=7 Hz); 1.20 (m, 2H); 0.92 (d, 6H, J=7 Hz).

EXAMPLE 16

(R)2-(4-isobutylphenyl)-N-[(N'-methyl,N'2-hydroxyethyl)-aminoethoxy]propionamide A solution of (R)2-(4-isobutylphenyl)propionyl chloride (0.42 g; 1.875 mmol) in $CH_2Cl_2$ (10 mL) is slowly added dropwise to a solution of 0.85 g (3.75 mmol) of 2-(amineoxy)-N-methyl-N-(2-hydroxyethyl)ethylamine in $CH_2Cl_2$ (10 mL) at 25° C. The mixture is kept under stirring at room temperature for 3 h, and then diluted with $H_2O$ (10 mL). The two phases are then shaken and the organic phase is separated, washed with water (5 mL), dried over $Na_2SO_4$ and evaporated to yield 0.59 g (1.43 mmol). of (R)2-(4-isobutylphenyl)-N-2-[(N'-methyl,N'2-hydroxyethyl)-aminoethoxy]propionamide as an oil.
$[\alpha]_D$=−35 (c=1; $CH_3OH$).
$^1$H-NMR ($CDCl_3$): δ 7.25 (m, 4H); 6.15 (bs, 1H, CONH); 4.67 (t, 2H, J=7 Hz); 3.40 (m, 2H); 2.75 (t, 2H, J=7 Hz); 2.55 (d, 2H, J=7 Hz); 2.35 (bs, 1H, OH); 2.42 (t, 2H, J=7 Hz); 2.21 (s, 3H); 1.95 (m, 1H); 1.53 (d, 3H, J=7 Hz); 1.00 (d, 6H, J=7 Hz).

EXAMPLE 17

R-2-[(4-isobutyl)phenyl]-N-[4-(dimethylamino)-2-butinyl]propionamide

R(−)-ibuprofen (0.34 g; 1.65 mmol) is dissolved in dry CH$_2$Cl$_2$; DCC (0.37 g; 1.8 mmol) and HOBZ (0.24 g; 1.78 mmol) are added and the solution is left at r.t under stirring. for 3 hrs. N,N-dimethylbutin-2-yl-1,4-diamine (0.2 g; 1.78 mmol) dissolved in dry CH$_2$Cl$_2$ (2 mL) is added to the solution and the resulting mixture is stirred overnight. After 18 hrs, DCU is filtered off and the filtrate is diluted with CH$_2$Cl$_2$, washed with sat. sol. NaHCO$_3$ (2×10 mL), water (2×10 mL) and brine, dried over Na$_2$SO$_4$ and evaporated under vacuum to give a red oily crude residue. The following purification by flash chromatography gives R(−)-2-[(4'-isobutyl)phenyl]-N-[4-(dimethylamino)-2-butinyl]propionamide as a yellow oil (0.347; 1.155 mmol).

[α]$_D$=+4.4 (c=0.5;CH$_3$OH)
$^1$H-NMR (CDCl$_3$): δ 7.15-7.10 (m, 2H); 7.09-7.05 (m, 2H); 5.45 (bs, 1H, CONH); 4.05 (m, 2H); 3.55 (m, 1H); 3.15 (s, 2H); 2.47 (d, 2H, J=7 Hz); 2.22 (s, 6H); 1.85 (m, 1H); 1.48 (d, 3H, J=7 Hz); 0.91 (d, 6H, J=7 Hz).

EXAMPLE 18

R-Z-2-[(4-isobutyl)phenyl]-N-[4-(dimethylamino)-2-butenyl]propionamide

R-2-[(4'-isobutyl)phenyl]-N-[4-dimethylamino-2-butinyl]propionamide of example 17 (0.08 g; 0.27 mmol) is dissolved in abs. EtOH (5 mL) and 5% Palladium on calcium carbonate (Lindlar catalyst; 0.08 g) is added. The mixture is hydrogenated under atmospheric pressure at r.t. for 2 hrs, then is filtered over a Celite pad. The filter cake is deeply washed with EtOH, the filtrate is evaporated under vacuum to give pure R-Z-2-[(4-isobutyl)phenyl]-N-[4-(dimethylamino)-2-butenyl]propionamide as pale yellow oil (0.07 g; 0.23 mmol)

[α]$_D$=−26.5 (c=1.1;CH$_3$OH)
$^1$H-NMR (CDCl$_3$): δ 7.20-7.12 (d, 2H, J=8 Hz); 7.10-7.05 (d, 2H, J=8 Hz); 5.95 (bs, 1H, CONH); 5.67-5.55 (m, 2H); 3.93-3.85 (m, 2H); 5.02 (m, 1H); 3.05 (d, 2H J=8 Hz); 2.47 (d, 2H, J=7 Hz); 2.25 (s, 6H); 1.93 (m, 1H); 1.55 (d, 3H, J=7 Hz); 0.95 (d,6H, J=7 Hz).

EXAMPLE 19

R-2-[(4-isobutyl)phenyl]-N-[4-(dimethylaminomethyl)phenyl]propionamide

R(−)Ibuprofen (0.31 g; 1.5 mmol) is dissolved in thionyl chloride (5 mL) and the solution is refluxed for 90'. The complete disappearance of starting carboxylic acid is monitored by IR; after cooling at room temperature and solvent stripping by 1.4-dioxane additions, the oily residue is diluted with dry DMF (5 mL) and added dropwise to a stirred solution of 4-(N,N-dimethylaminomethyl)aniline (0.27 g; 1.8 mmol) in dry DMF (3 mL) at room temperature. The solution is left under stirring overnight; the solvent evaporated under vacuum and the residue purified by flash chromatography to give R2-[(4-isobutyl)phenyl]-N-[4-(dimethylaminomethyl)phenyl]propionamide as a pale yellow oil (0.406 g; 1.2 mmol).

[α]$_D$=−98 (c=1;CH$_3$OH)
$^1$H-NMR (CDCl$_3$): δ 7.40-7.18 (m, 9H); 3.75 (m, 1H); 3.47 (s, 2H); 2.50 (d, 2H, J=7 Hz); 2.17 (s, 6H); 1.95 (m, 1H); 1.56 (d, 3H, J=7 Hz); 0.94 (d, 6H, J=7 Hz).

Following the same procedure R-2-[(4-isobutyl)phenyl]-N-[4-(dimethylamino)phenyl]propionamide has been prepared.

[α]$_D$=−131 (c=0.25;CH$_3$OH)
$^1$H-NMR (CDCl$_3$): δ 7.28-7.25 (m, 4H); 7.22-7.15 (m, 2H); 6.83-6.79 (bs, 1H, CONH); 6.73-6.65 (m, 2H); 3.72 (m, 1H); 2.80 (s, 6H); 2.48 (d, 2H, J=7 Hz); 1.85 (m, 1H); 1.52 (d, 3H, J=7 Hz); 0.97 (d, 6H, J=7 Hz).

TABLE I

| Example | Structure | % Inhibition of IL-8 induced (10 ng/mL) PMNs Chemotaxis | % Inhibition of C5a induced (1 ng/mL) PMNs Chemotaxis |
|---|---|---|---|
| (R),(S')-2-(4'-isobutylphenyl)-N-(1-carboxy-5-aminopentyl)propionamide hydrochloride | 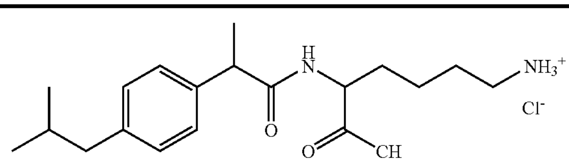 | 10$^{-8}$M 5 ± 8 | 10$^{-5}$M 49 ± 3 |
| (S'),(R)-2-(4-isobutylphenyl)-N-[1-carboxy-4-(1-piperidinyl)butyl]propionamide sodium salt | 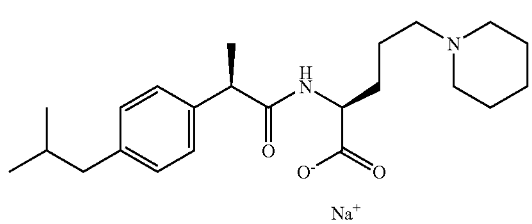 | 56 ± 9 | 33 ± 15 |
| (R)-2-(4-isobutylphenyl)-N-(2-dimethylaminoethyl) propionamide hydrochloride |  | 56 ± 13 | 62 ± 12 |

TABLE I-continued

| Example | Structure | % Inhibition of IL-8 induced (10 ng/mL) PMNs Chemotaxis | % Inhibition of C5a induced (1 ng/mL) PMNs Chemotaxis |
| --- | --- | --- | --- |
| (R)-2-(4-isobutylphenyl)-N-(3-dimethylamino-propyl) propionamide hydrochloride | 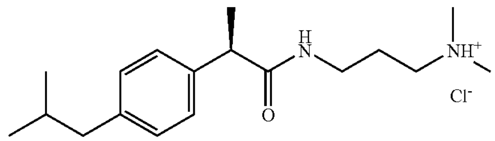 | 51 ± 15 | 65 ± 14 |
| (R)-2-(4-isobutylphenyl)-N-(3-aminopropyl) propionamide hydrochloride | 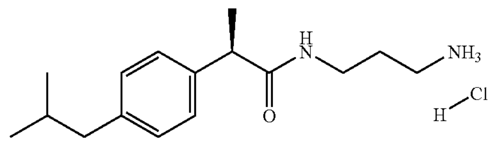 | 2 ± 7 | 84 ± 8 |
| (R)-2-(4-isobutylphenyl)-N-(4-dimethylamino-butyl) propionamide hydrochloride | 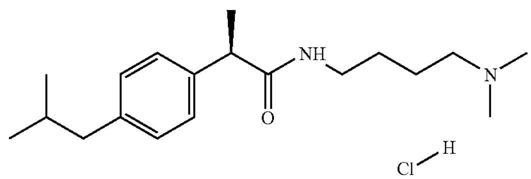 | 34 ± 6 | 55 ± 8 |
| (R)-2-(4-isobutylphenyl)-N-(1-methyl-piperidin-4-yl)propionamide hydrochloride | 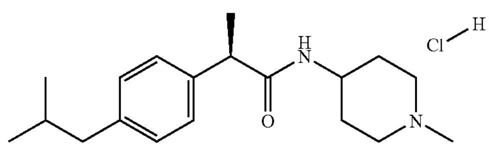 | 4 ± 9 | 48 ± 8 |
| (R)-2-(4-isobutylphenyl)-N-(exo-8-methyl-8-aza-bicyclo[3.2.1]oct-3-yl)propionamide hydrochloride | 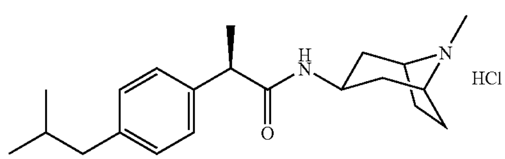 | 3 ± 8 | 57 ± 6 |
| (R)-2-(4-isobutylphenyl)-N-3-(N-morpholinyl propyl)propionamide hydrochloride | 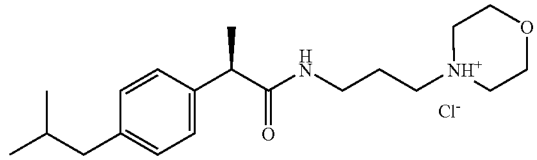 | 55 ± 12 | 24 ± 11 |
| (R)-2-(4-isobutylphenyl)-N-3-(1-piperidinylpropyl) propionamide hydrochloride | 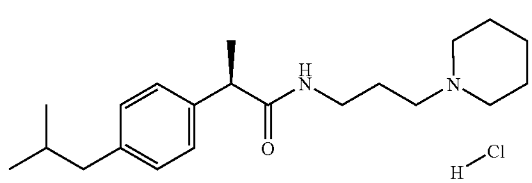 | 46 ± 8 | 76 ± 6 |
| (R)-2-(4-isobutyl)phenyl-N-[2-(dimethylaminoethyl) aminocarbonylmethyl]propionamide hydrochloride | 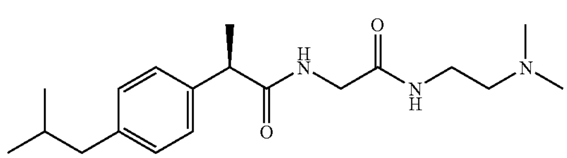 | 31 ± 6 | 68 ± 4 |
| (R)-2-(3-isopropylphenyl)-N-3-(dimethylaminopropyl) propionamide | 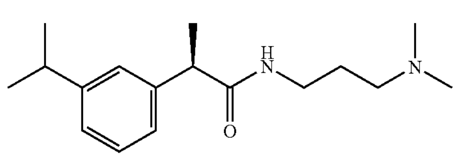 | 48 ± 2 (c = 10$^{-6}$M) | 42 ± 18 |

TABLE I-continued

| Example | Structure | % Inhibition of IL-8 induced (10 ng/mL) PMNs Chemotaxis | % Inhibition of C5a induced (1 ng/mL) PMNs Chemotaxis |
|---|---|---|---|
| (R)-2-(3-isopropylphenyl)-N-3-(dimethylaminopropyl) propionamide | 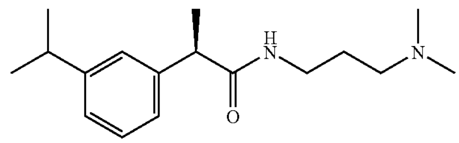 | 5 ± 6 | 42 ± 18 |
| (R)-2-(3-benzoylphenyl)-N-3-(dimethylamino propyl) propionamide | 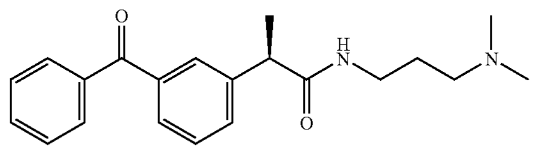 | 53 ± 8 | 56 ± 2 |
| (R)-2-[2-(2,6-dichlorophenylamino)phenyl]-N-3-(dimethylaminopropyl)propionamide | 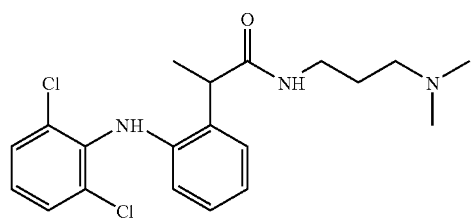 | 58 ± 5 (c = 10$^{-6}$M) | 41 ± 2 |
| (R)-2-[2-(2,6-dichlorophenylamino)-phenyl]-N-3-(dimethylaminopropyl)propionamide | 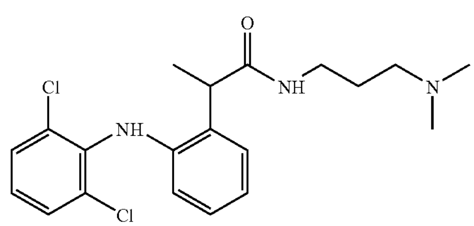 | 1 ± 13 | 41 ± 2 |

The invention claimed is:

1. A pharmaceutical composition consisting of (R)-2-Aryl-propionamide compound of formula (I)

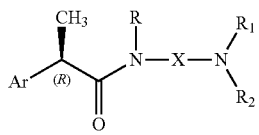

or a pharmaceutically acceptable salt thereof,
wherein
Ar is a group selected from 4-isobutylphenyl, 2-(2,6-dichloro-phenyl-amino)-phenyl, or a phenyl 3-substituted with a group selected from the group consisting of benzoyl, isopropyl, isobutyl, pent-3-yl, 1-phenyleth-ylen-1-yl, α-methylbenzyl, α-hydroxybenzyl, and α-hydroxyethyl,
R represents hydrogen,
X is a linear or branched C1-C6 alkylene,
R1 and R2 are:
independently hydrogen or methyl; or
R1 and R2 together with the N atom to which they are bound, form a 6 membered ring of formula (II) selected from the group consisting of 1-piperidinyl and morpholinyl

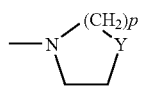

wherein the compound of the formula (I) has activity of inhibition of C5a-induced chemotaxis of polymorphonucleate leukocytes and monocytes and is devoid of any significant activity of inhibition of a cyclooxygenase enzyme.

2. The composition according to claim 1, in which the compound of the formula I has activity as an inhibitor of IL-8 induced chemotaxis of polymorphonucleate leukocytes.

3. The composition of claim 1, wherein X is a C2-C4 alkylene.

4. The composition according to claim 1 wherein said compound of formula (I) is selected from the group consisting of:
(R)-2-[(4-isobutyl)phenyl]-N-(2-dimethylaminoethyl) propionamide;
(R)-2-[(4-isobutyl)phenyl]-N-(3-dimethylaminopropyl) propionamide;
(R)-2-[(4-isobutyl)phenyl]-N-(3-aminopropyl)propionamide;
(R)-2-[(4-isobutyl)phenyl]-N-(4-dimethylaminobutyl)-propionamide;

(R)-2-[(4-isobutyl)phenyl]-N-3-(N-morpholinylpropyl) propionamide;
(R)-2-[(4-isobutyl)phenyl]-N-3-(1-piperidinylpropyl)propionamide;
(R)-2-[(3-isopropyl)phenyl]-N-(3-dimethylaminopropyl) propionamide;
(R)-2-(3-benzoylphenyl)-N-3-(dimethylaminopropyl) propionamide;
2-[2-(2,6-dichlorophenylamino)-phenyl]-N-3-(dimethylaminopropyl)propionamide.

5. The composition according to claim 1 wherein said compound of formula (I) is selected from the group consisting of:
(R)-2-(4-isobutylphenyl)-N-(3-dimethylamino-propyl) propionamide hydrochloride,
(R)-2-(4-isobutylphenyl)-N-3-(1-piperidinylpropyl)propionamide hydrochloride, and
(R)-2-(3-benzoylphenyl)-N-3-(dimethylamino-propyl) propionamide.

* * * * *